(12) United States Patent
Drnek et al.

(10) Patent No.: US 12,636,183 B2
(45) Date of Patent: May 26, 2026

(54) COOLING SYSTEMS, DEVICES, AND RELATED METHODS

(71) Applicant: Neuraxis, LLC, Sandown, NH (US)

(72) Inventors: Michael Drnek, Hampstead, NH (US); Dan Farley, Traverse City, MI (US)

(73) Assignee: Neuraxis, LLC, Sandown, NH (US)

( * ) Notice: Subject to any disclaimer, the term of this patent is extended or adjusted under 35 U.S.C. 154(b) by 692 days.

(21) Appl. No.: 17/476,059

(22) Filed: Sep. 15, 2021

(65) Prior Publication Data

US 2022/0000659 A1 Jan. 6, 2022

Related U.S. Application Data

(63) Continuation-in-part of application No. PCT/US2020/022974, filed on Mar. 16, 2020.
(Continued)

(51) Int. Cl.
*A61F 7/12* (2006.01)
*A61B 17/02* (2006.01)
*A61F 7/00* (2006.01)

(52) U.S. Cl.
CPC ............ *A61F 7/12* (2013.01); *A61B 17/0206* (2013.01); *A61B 2017/0212* (2013.01);
(Continued)

(58) Field of Classification Search
CPC ........ A61F 2007/126; A61F 2007/0054–0069; A61F 2007/0075–0076;
(Continued)

(56) References Cited

U.S. PATENT DOCUMENTS

| | | | |
|---|---|---|---|
| 7,959,657 B1 * | 6/2011 | Harsy .................... | A61F 7/007 607/104 |
| 2004/0077931 A1 * | 4/2004 | Larnard ................ | A61B 17/02 600/201 |

(Continued)

FOREIGN PATENT DOCUMENTS

EP 1321117 A2 * 6/2003 ............. A61F 7/007

OTHER PUBLICATIONS

International Preliminary Report on Patentability, received in PCT Application No. PCT/US2020/022974, Sep. 16, 2021, 6 pages.

*Primary Examiner* — Linda C Dvorak
*Assistant Examiner* — Davina E. Lee
(74) *Attorney, Agent, or Firm* — Hayes Soloway P.C.

(57) ABSTRACT

Cooling systems are described herein that may be used in connection with one or more attached devices to cool patient tissue. The disclosed cooling systems include a refrigeration unit containing a thermoelectric element in thermal communication with a heat exchanger, a fluid pump in fluid communication with a fluid inlet and a fluid outlet, tubing connecting the fluid inlet to the fluid outlet, a fluid cooling element in thermal contact with the thermoelectric element, and a temperature sensor positioned to detect a temperature of fluid within the tubing. The temperature of fluid within the tubing can be controlled by a control unit having a user interface and a power controller to adjust cooling power to the thermoelectric element. Various types of devices can be configured to receive and circulate cooled fluid from the cooling systems, such as retractor blades, retractor shims, cooling pads, and scope sheaths.

20 Claims, 40 Drawing Sheets

Related U.S. Application Data

(60) Provisional application No. 62/818,921, filed on Mar. 15, 2019.

(52) U.S. Cl.
CPC ................ *A61B 2017/0262* (2013.01); *A61F 2007/0056* (2013.01); *A61F 2007/0095* (2013.01); *A61F 2007/126* (2013.01)

(58) Field of Classification Search
CPC .. A61F 2007/0095–0096; A61F 7/0085; A61F 7/12; A61B 17/02; A61B 17/0206; A61B 17/0218; A61B 17/025; A61B 17/0281; A61B 2017/0212; A61B 2017/0225; A61B 2017/0256; A61B 2017/0268; A61B 2017/0275; A61B 2018/00565; A61B 5/6878; A61B 17/56; A61B 17/58; A61B 17/68–90
See application file for complete search history.

(56) References Cited

U.S. PATENT DOCUMENTS

| | | | |
|---|---|---|---|
| 2007/0112401 A1 | 5/2007 | Balachandran et al. | |
| 2007/0129707 A1* | 6/2007 | Blott ...................... | A61F 13/05 604/308 |
| 2008/0228248 A1* | 9/2008 | Guyuron ................... | A61F 7/02 607/108 |
| 2012/0179230 A1 | 7/2012 | Barrones et al. | |
| 2015/0080952 A1* | 3/2015 | Drnek ..................... | A61F 7/123 606/279 |
| 2016/0354234 A1* | 12/2016 | Dabrowiak ........... | A61F 7/0085 |
| 2018/0207024 A1* | 7/2018 | Dabrowiak ........... | A61F 7/0085 |
| 2018/0280191 A1* | 10/2018 | Taylor ................... | A61F 7/0053 |
| 2018/0296389 A1 | 10/2018 | Robst et al. | |
| 2022/0313481 A1* | 10/2022 | Dabrowiak ............. | A61F 7/123 |

* cited by examiner

202
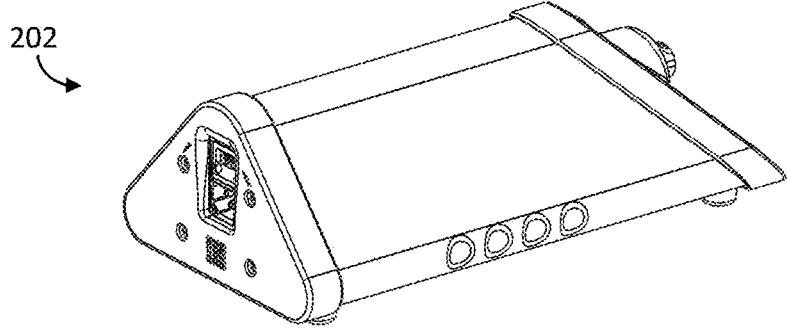
FIG. 2H(i)
202
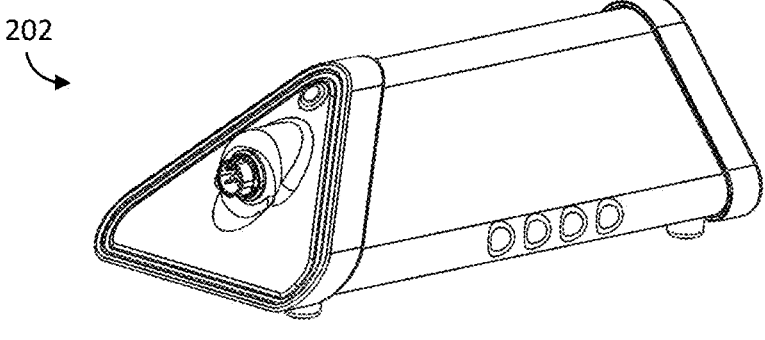
FIG. 2H(ii)

201
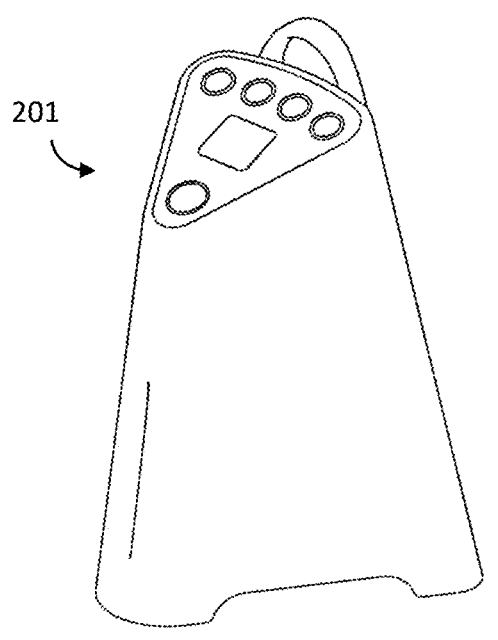
FIG. 2I(i)
112
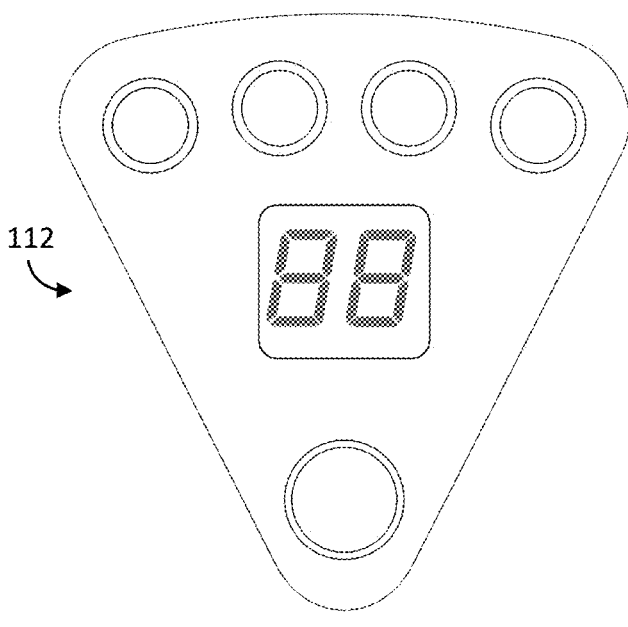
FIG. 2I(ii)

105
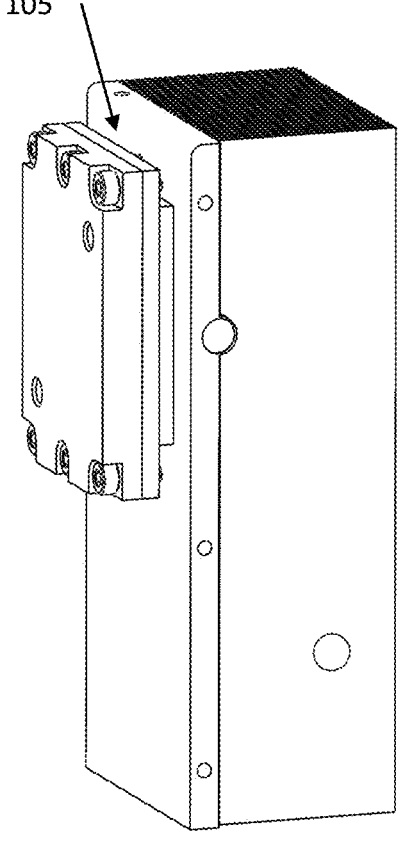
FIG. 2J(i)
105
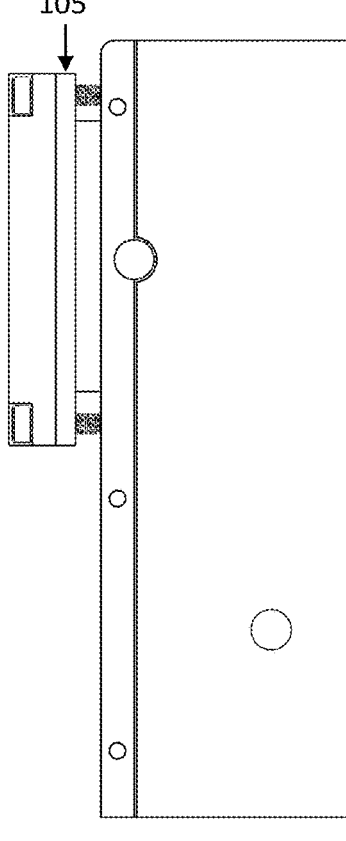
FIG. 2J(ii)

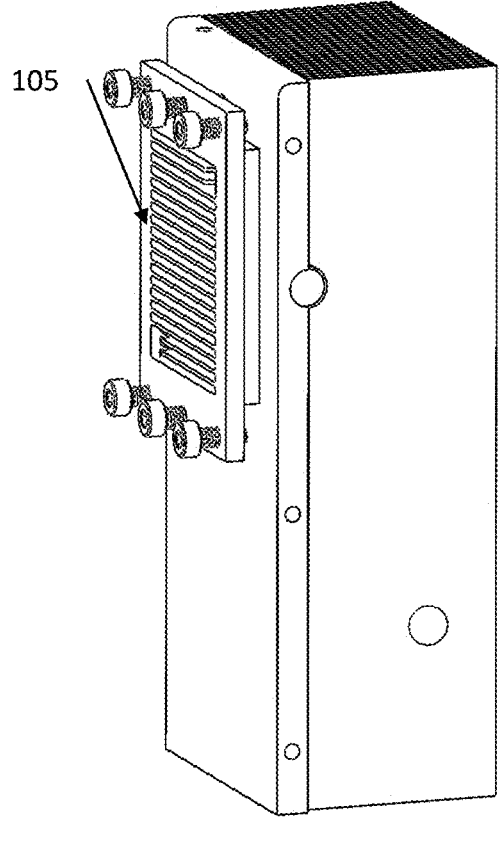
105
FIG. 2J(iii)
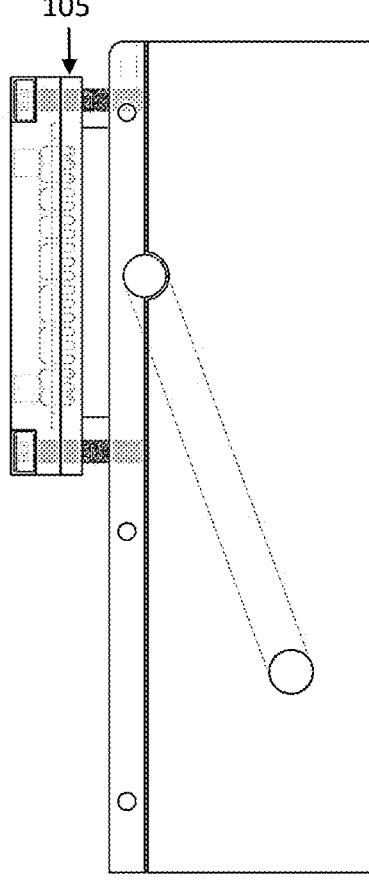
105
FIG. 2J(iv)

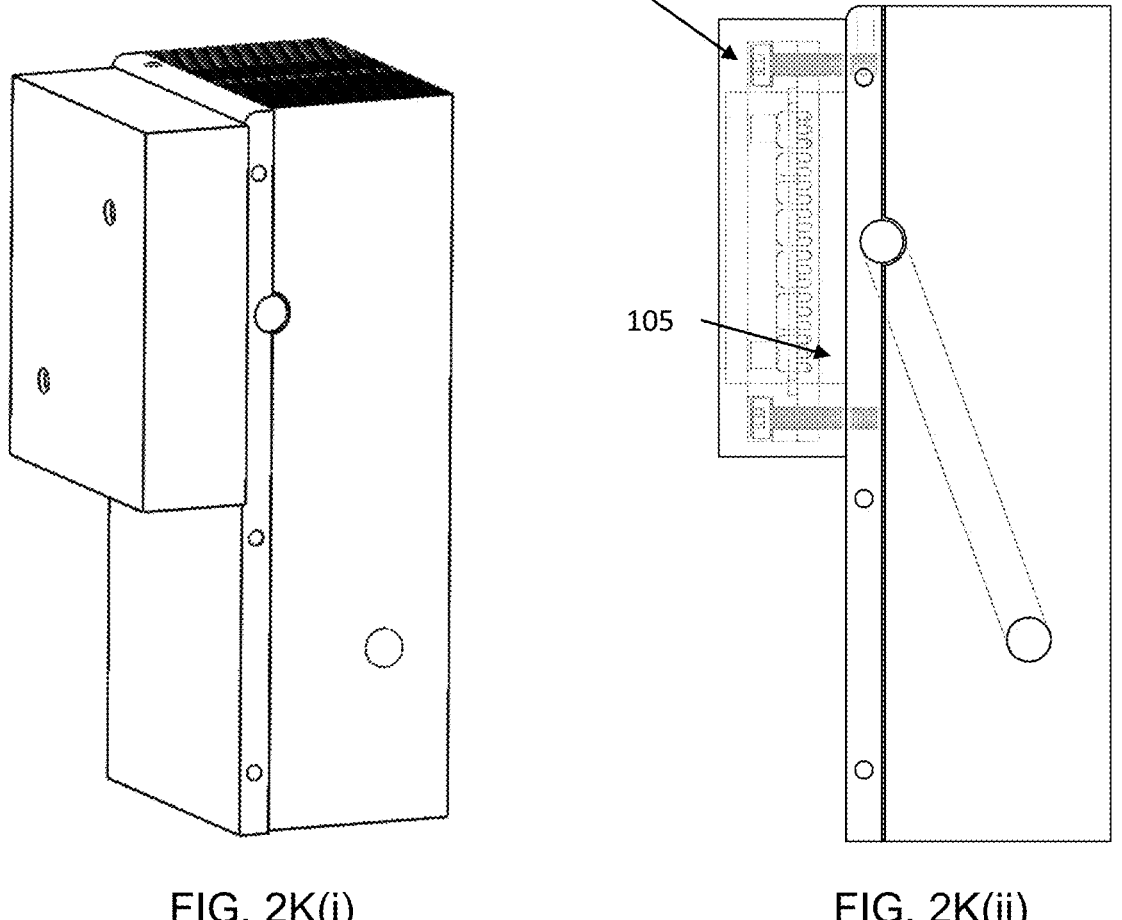
FIG. 2K(i)                                FIG. 2K(ii)

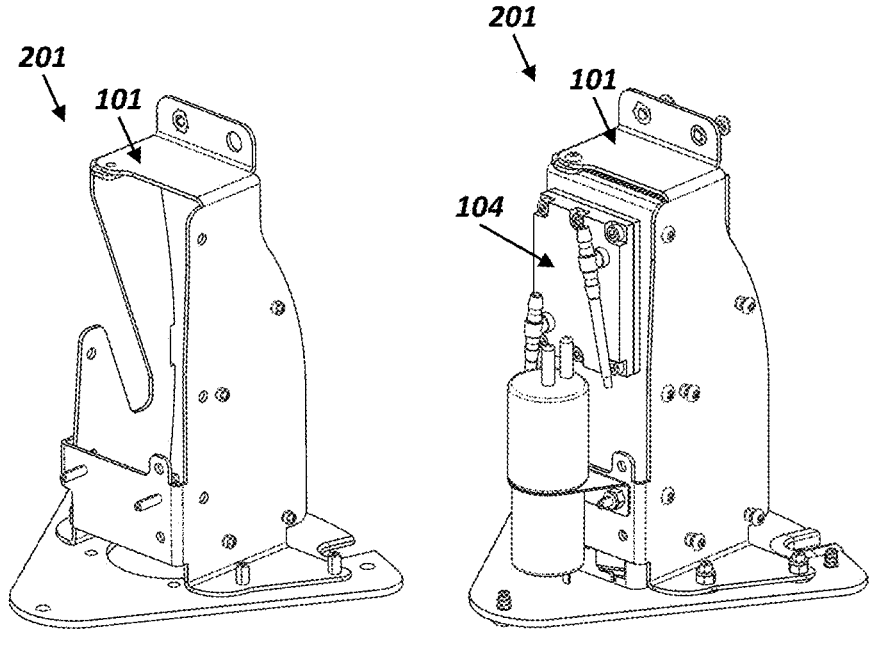
FIG. 2L(i)                    FIG. 2L(ii)
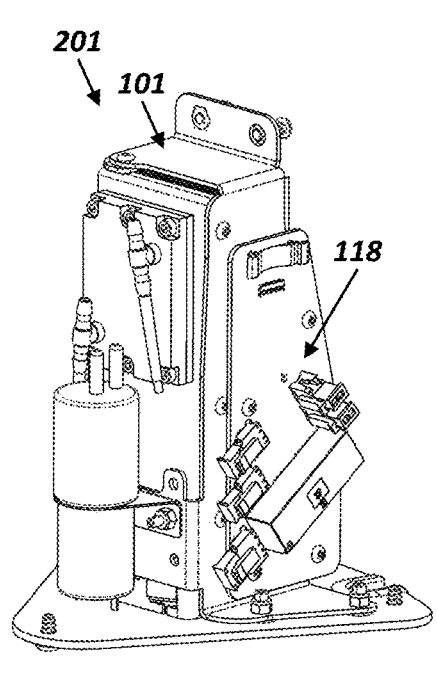
FIG. 2L(iii)

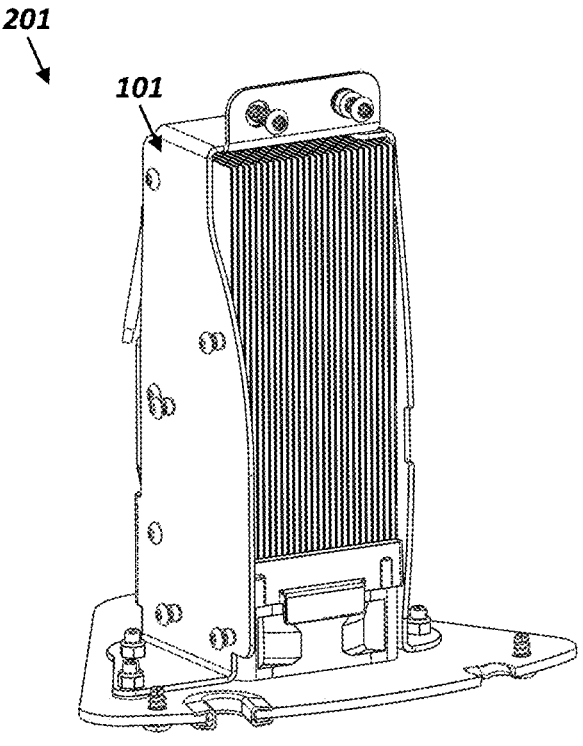
FIG. 2L(iv)
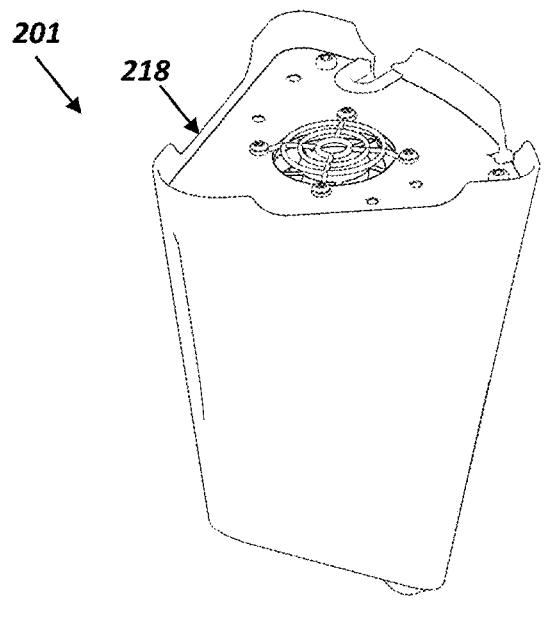
FIG. 2L(v)

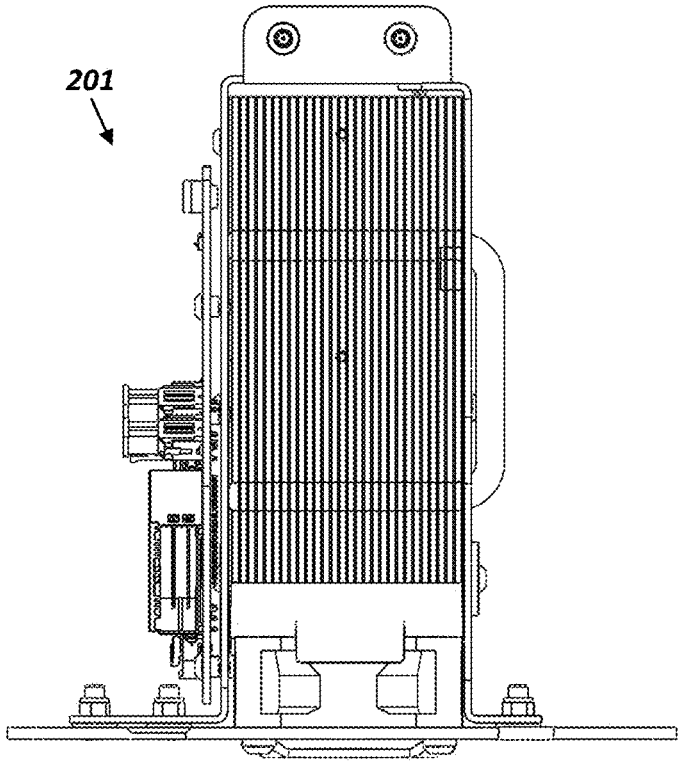
FIG. 2L(vi)

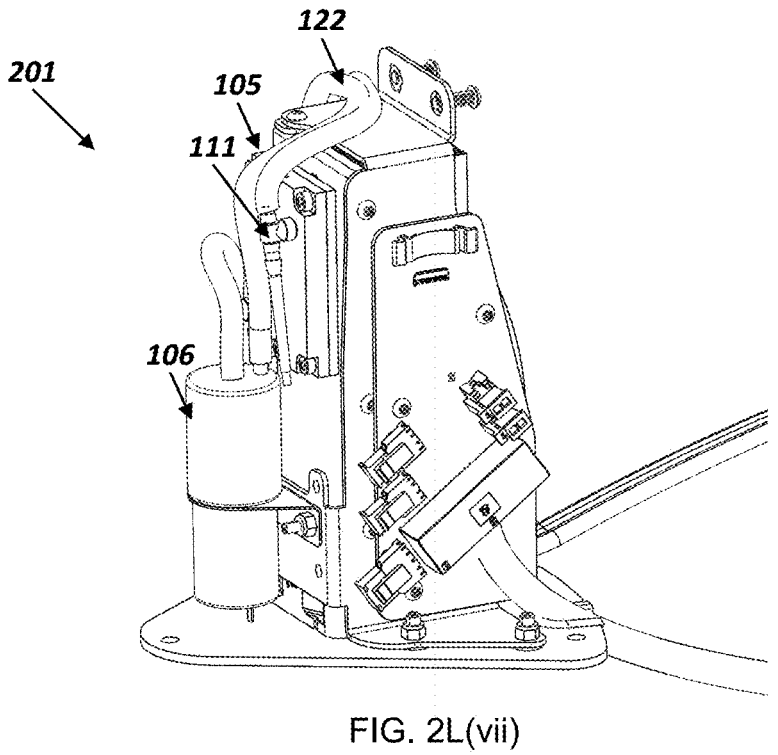
FIG. 2L(vii)
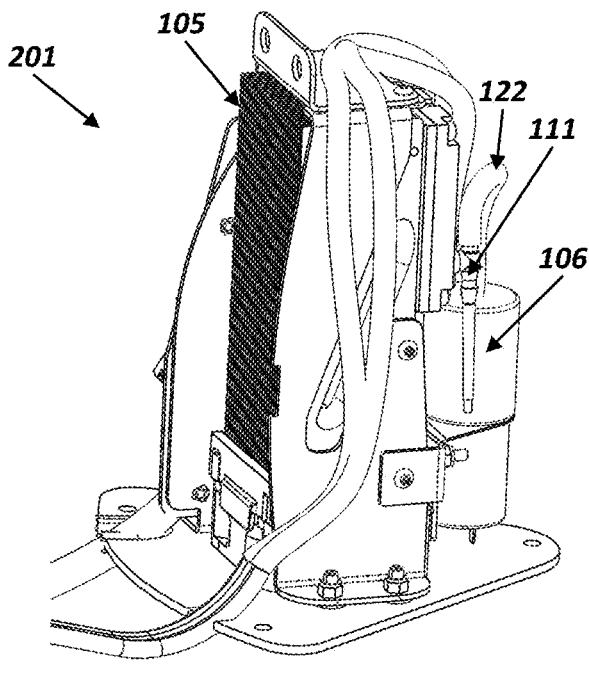
FIG. 2L(viii)

FIG. 2M (ii)

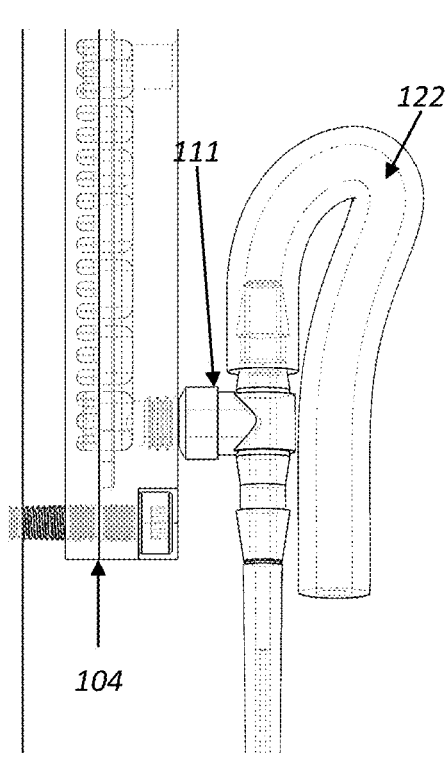
FIG. 2M (iii)
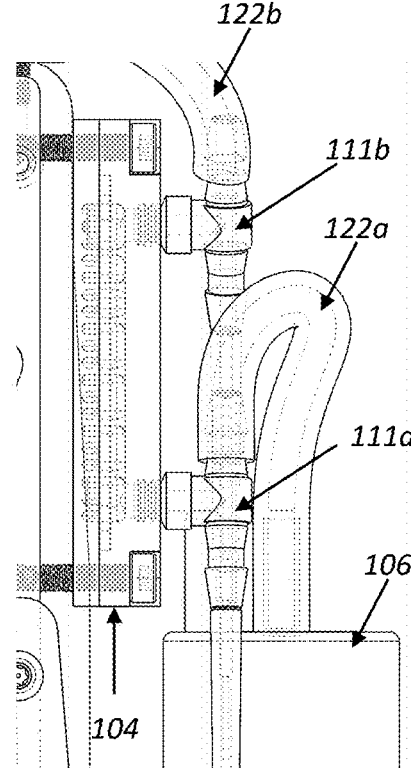
FIG. 2M (iv)

*111*
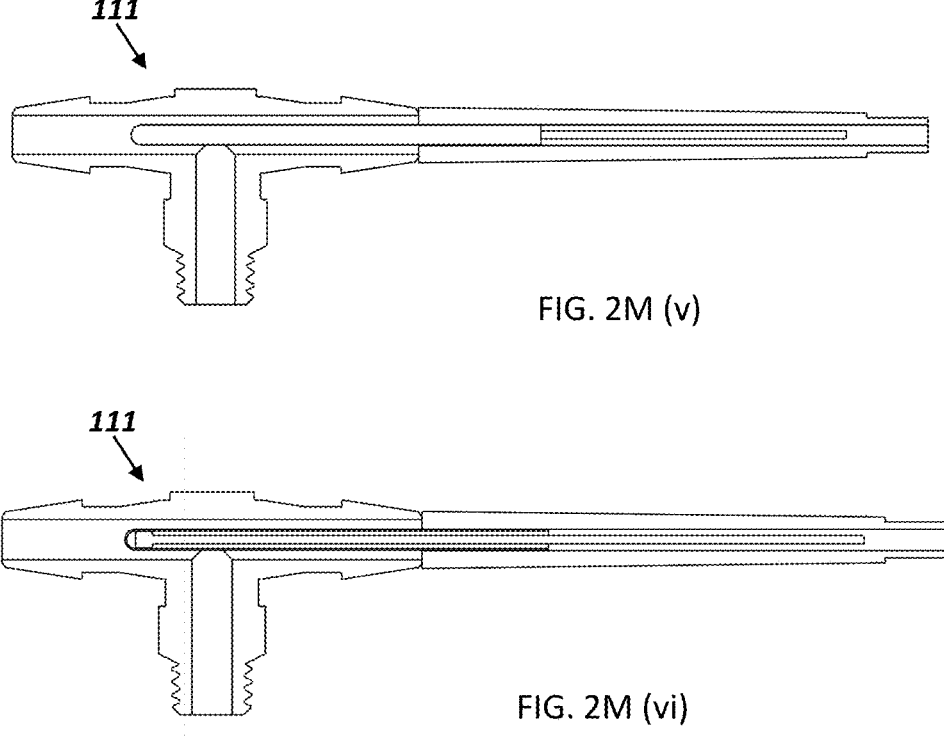
FIG. 2M (v)
*111*
FIG. 2M (vi)
*111*
FIG. 2M (vii)

FIG. 4A(iii)

FIG. 4B(iii)

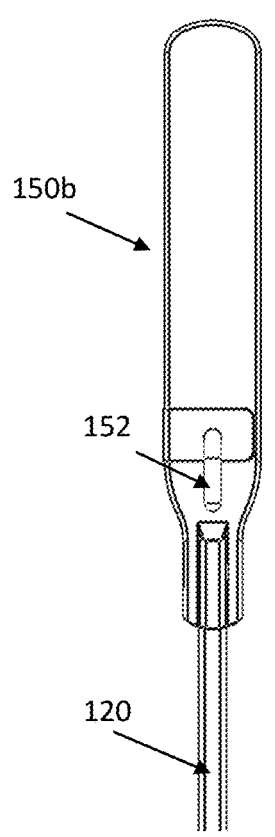
FIG. 5A(i)
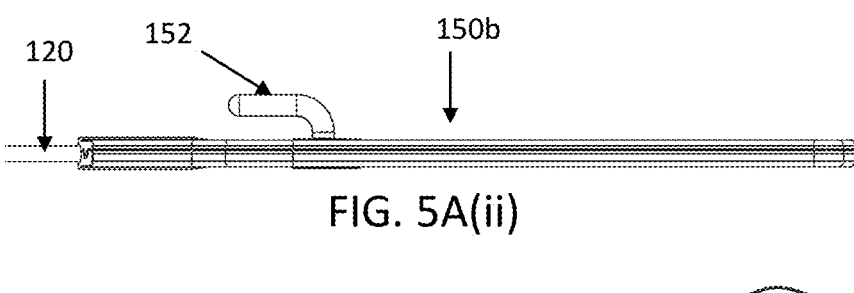
FIG. 5A(ii)
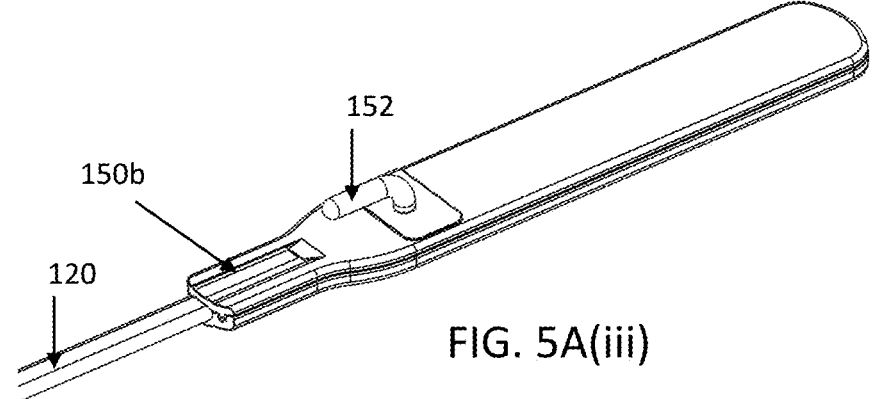
FIG. 5A(iii)

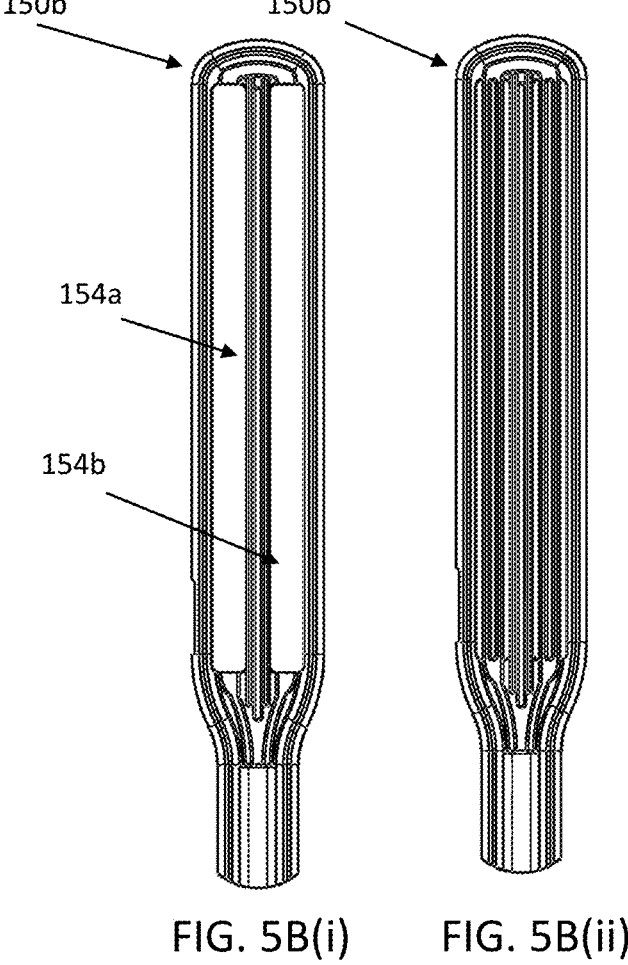
FIG. 5B(i)    FIG. 5B(ii)
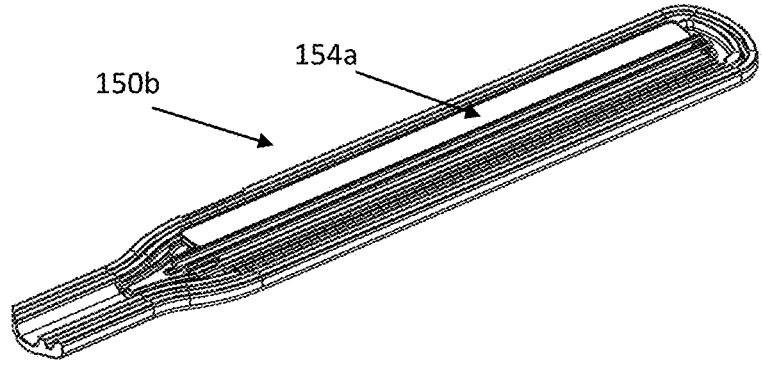
FIG. 5B(iii)

FIG. 5C(iii)

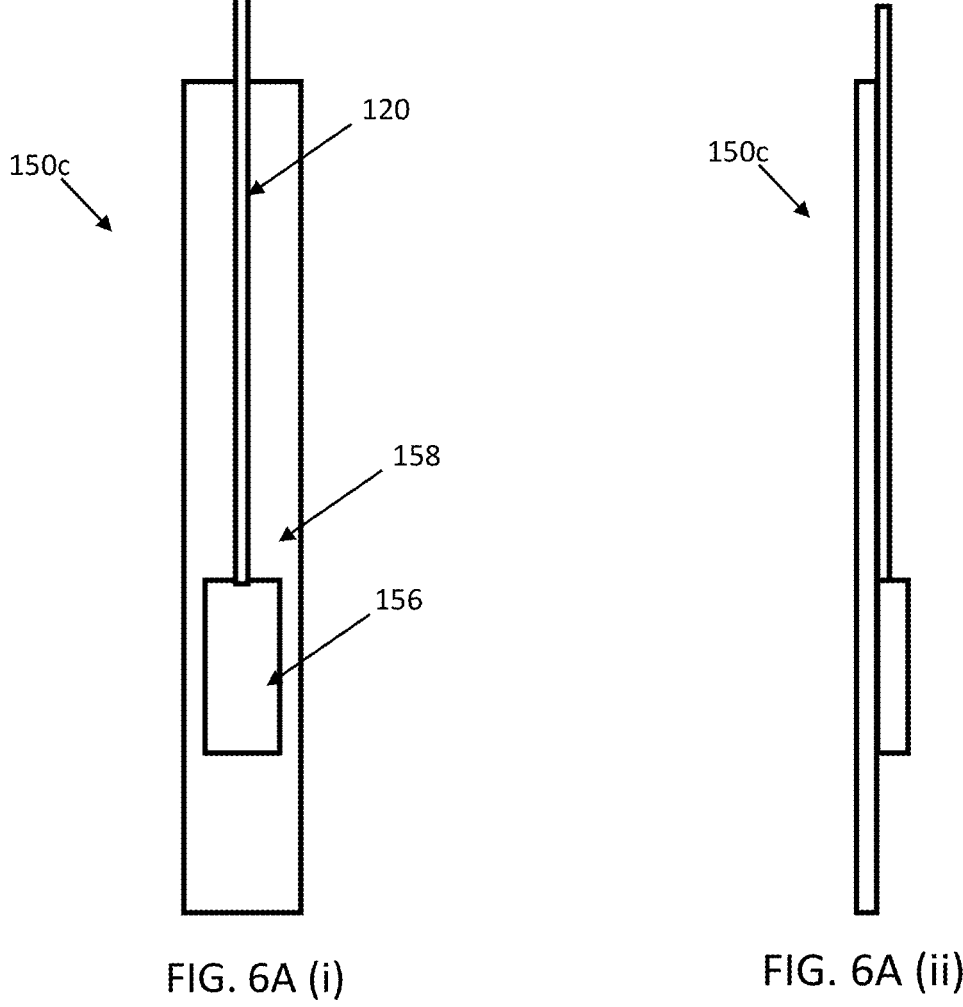
FIG. 6A (i)                    FIG. 6A (ii)

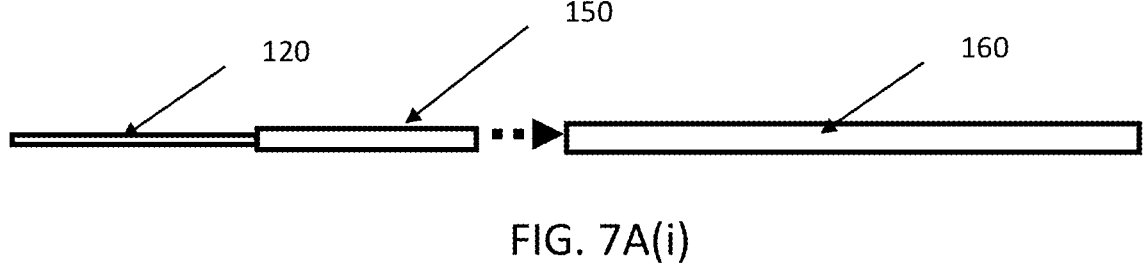
FIG. 7A(i)
FIG. 7A(ii)

160
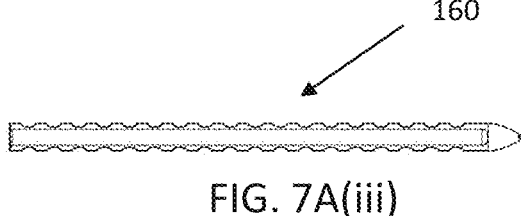
FIG. 7A(iii)
160
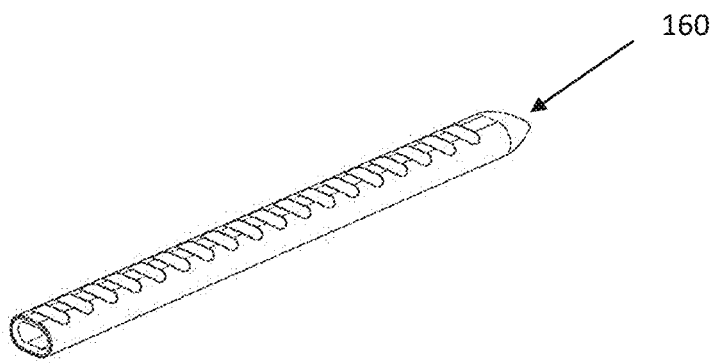
FIG. 7A(iv)

FIG. 8A(ii)

FIG. 8A(iii)

FIG. 8A(iv)

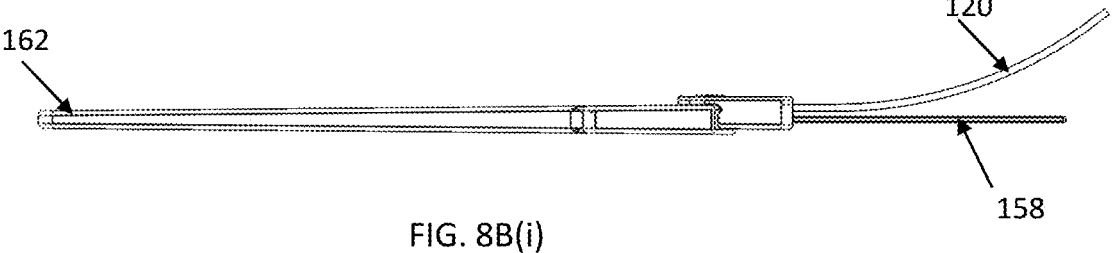
FIG. 8B(i)
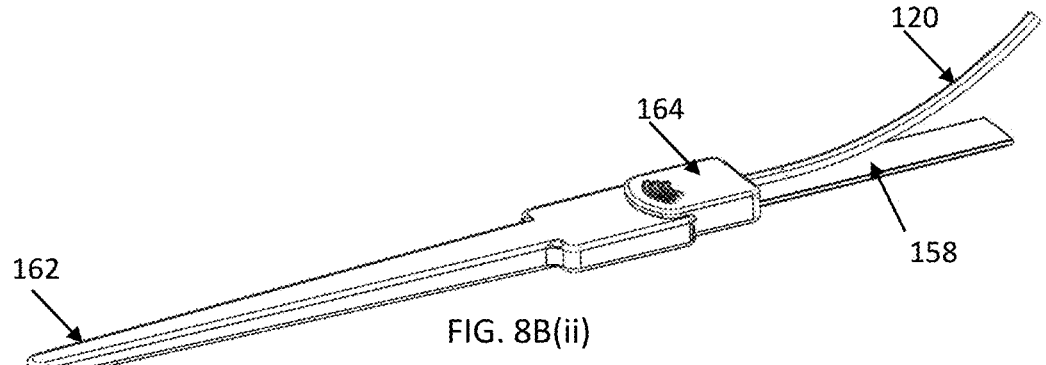
FIG. 8B(ii)

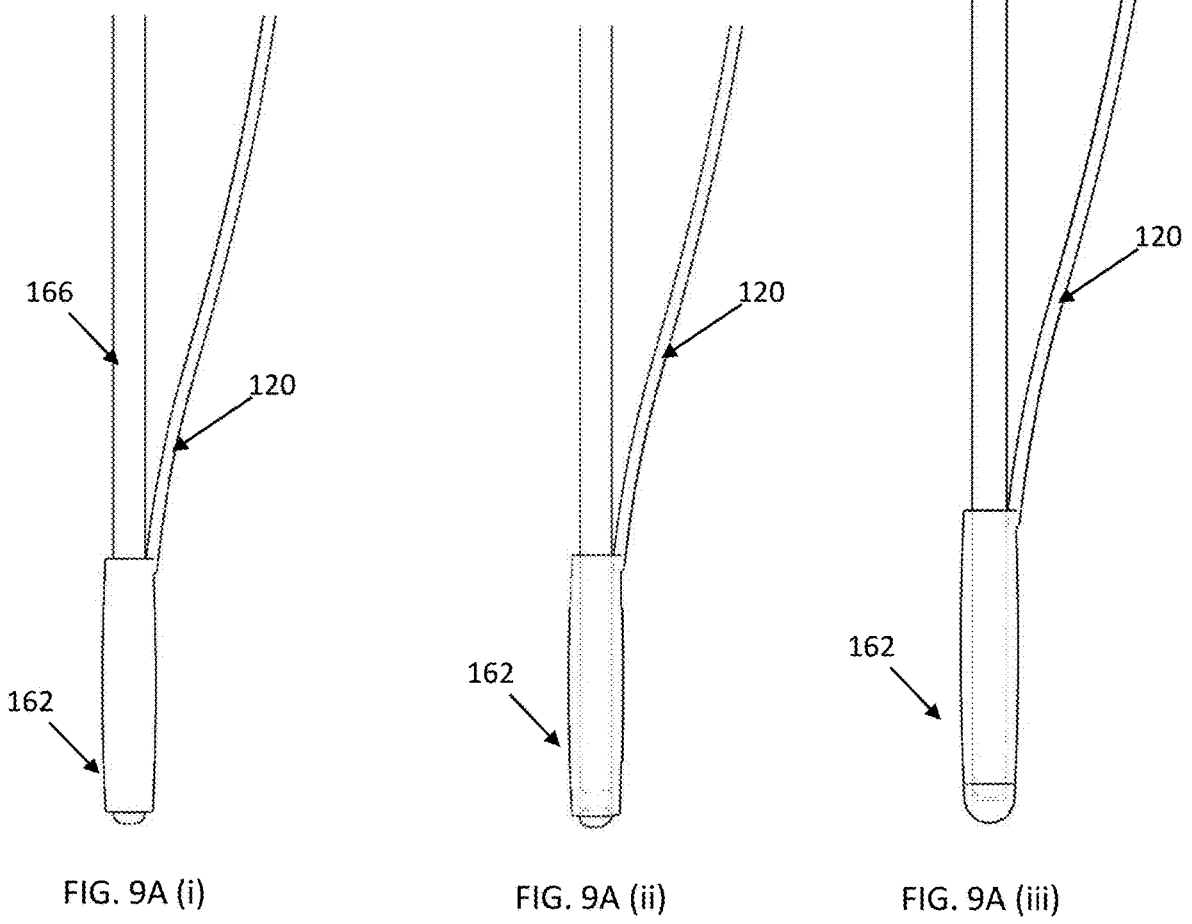
FIG. 9A (i)          FIG. 9A (ii)          FIG. 9A (iii)

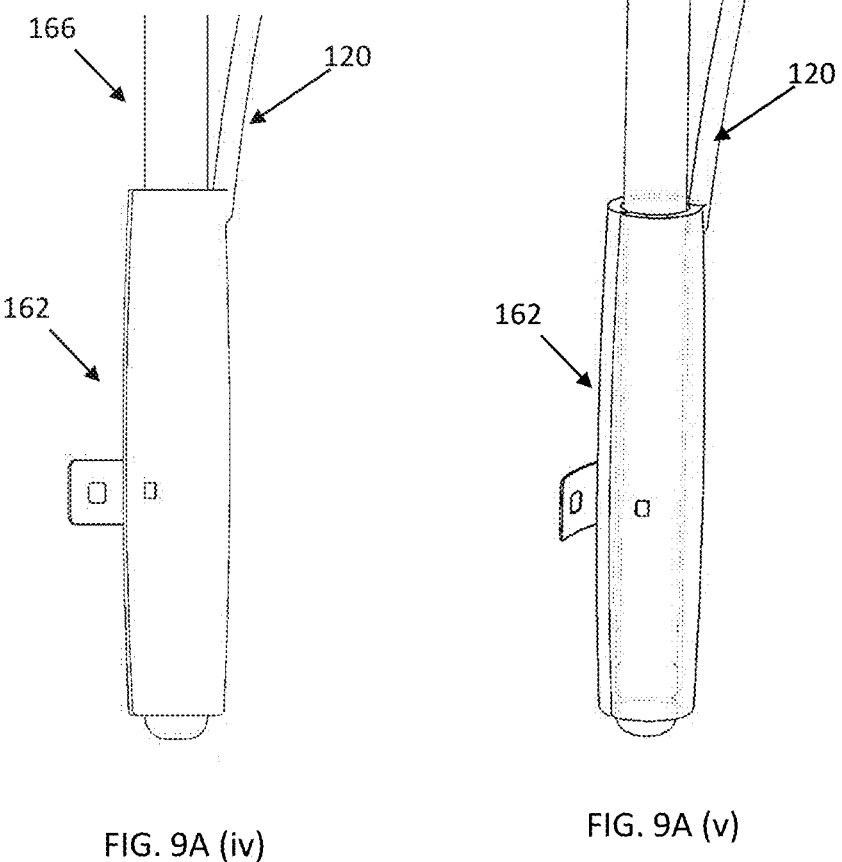
FIG. 9A (iv)                    FIG. 9A (v)

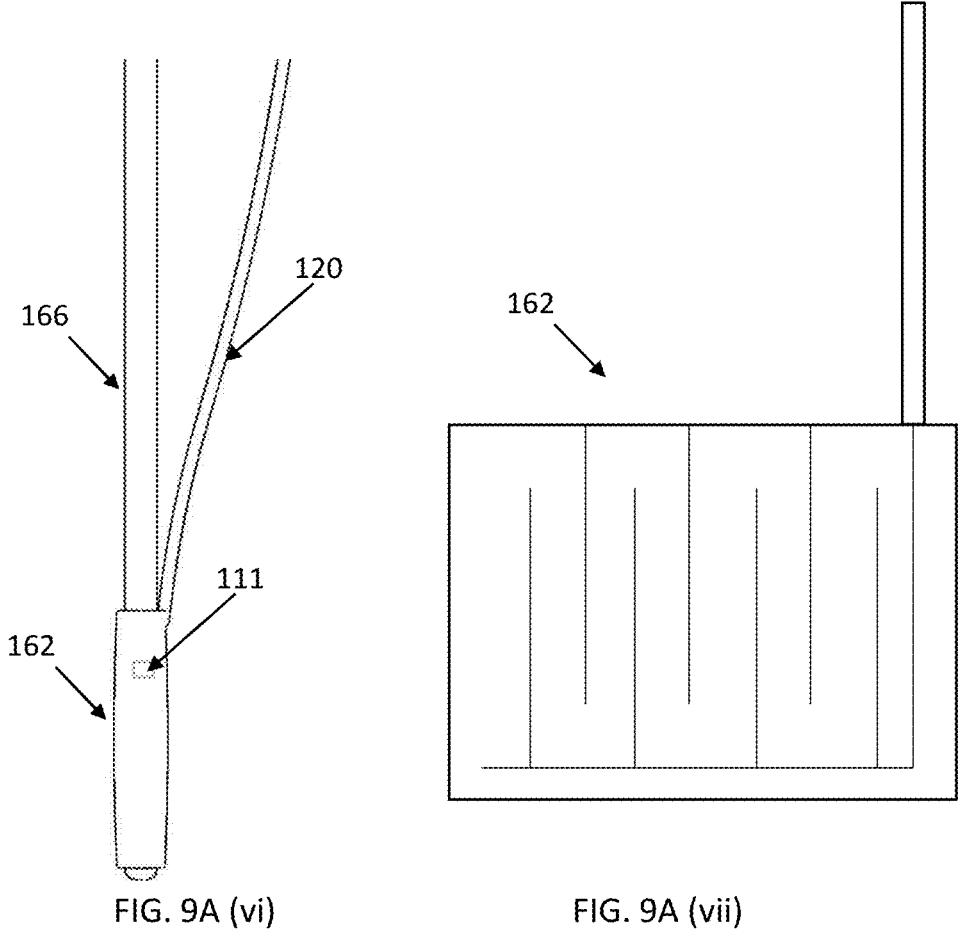
FIG. 9A (vi)           FIG. 9A (vii)

150d
168          120
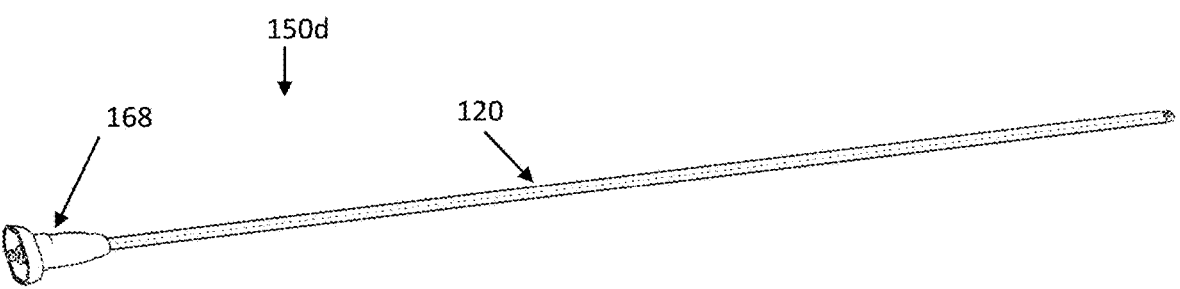
FIG. 10A (i)
150d          150d
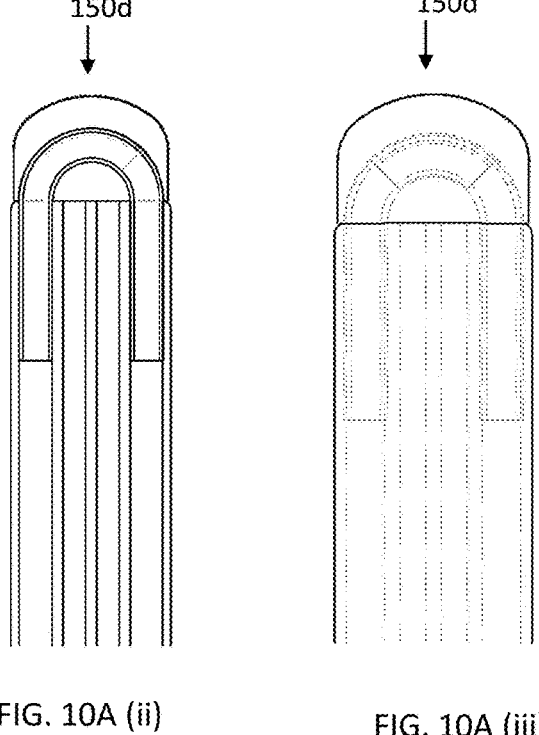
FIG. 10A (ii)          FIG. 10A (iii)

150d
168
120
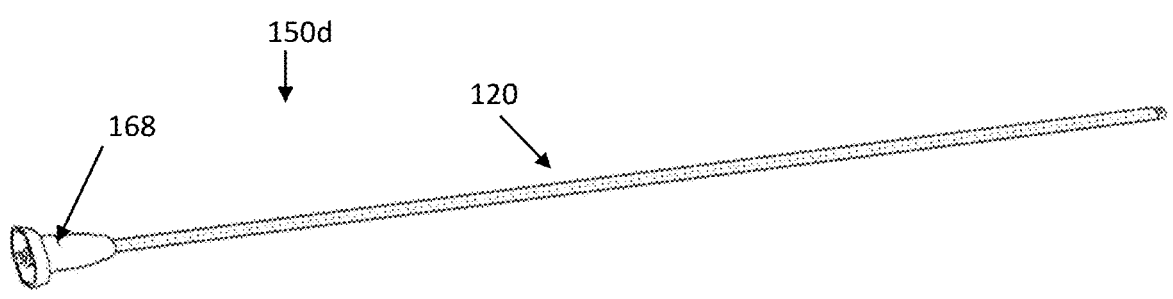
FIG. 10B (i)
150d
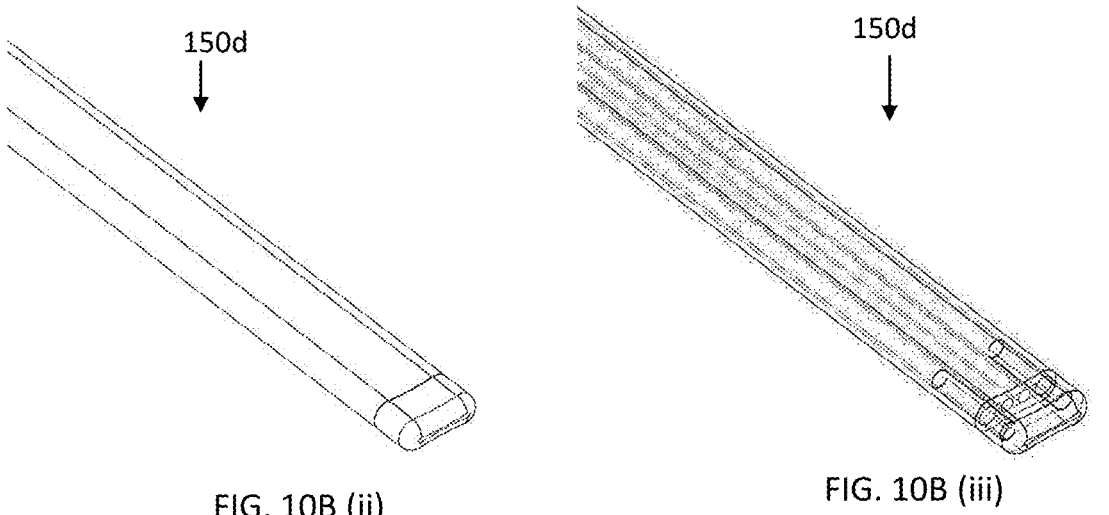
150d
FIG. 10B (ii)
FIG. 10B (iii)

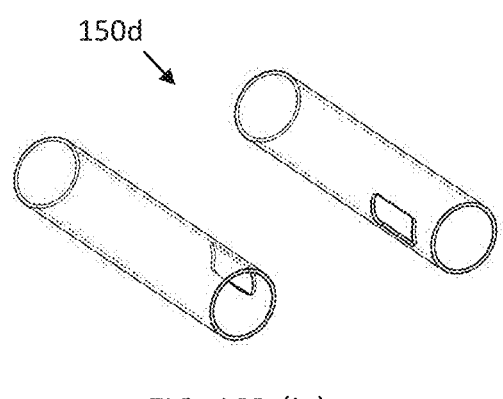
FIG. 10B (iv)
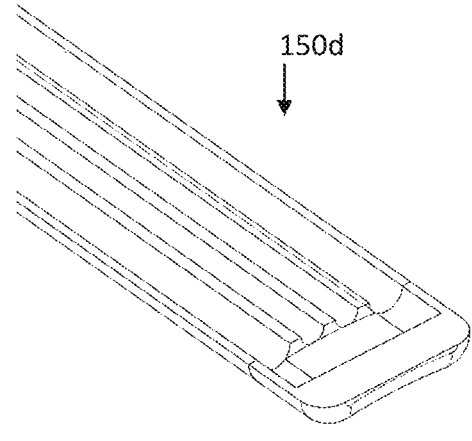
FIG. 10B (v)
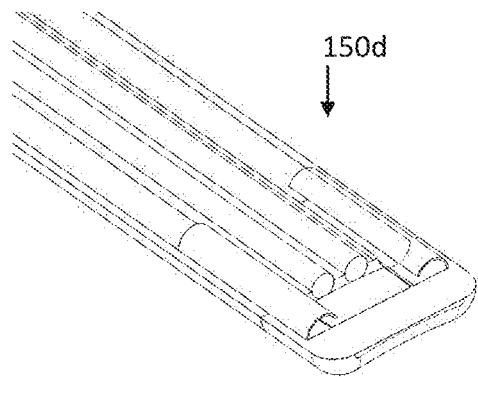
FIG. 10B (vi)
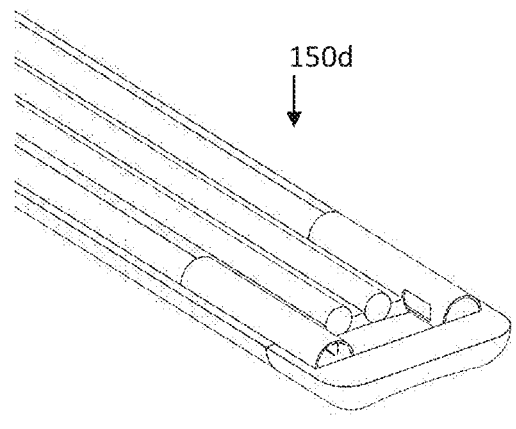
FIG. 10B (vii)

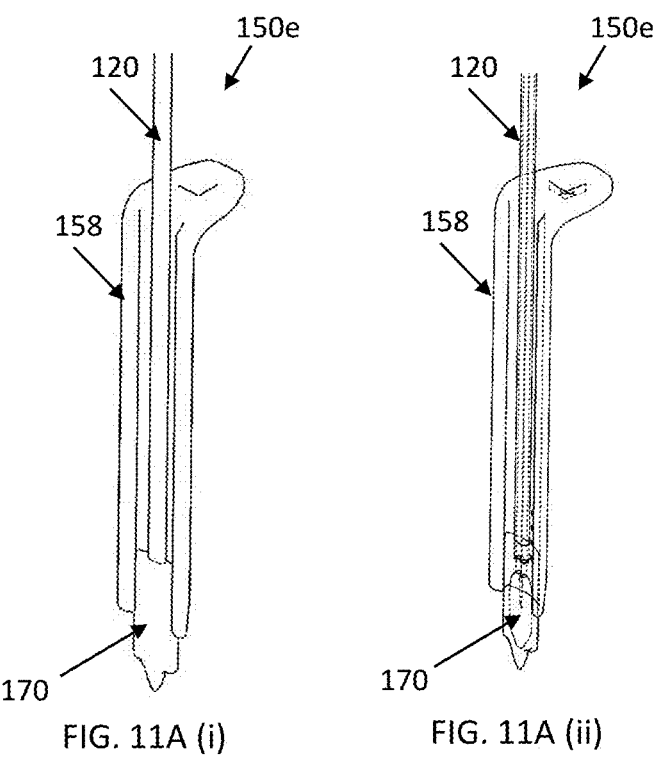
FIG. 11A (i)          FIG. 11A (ii)
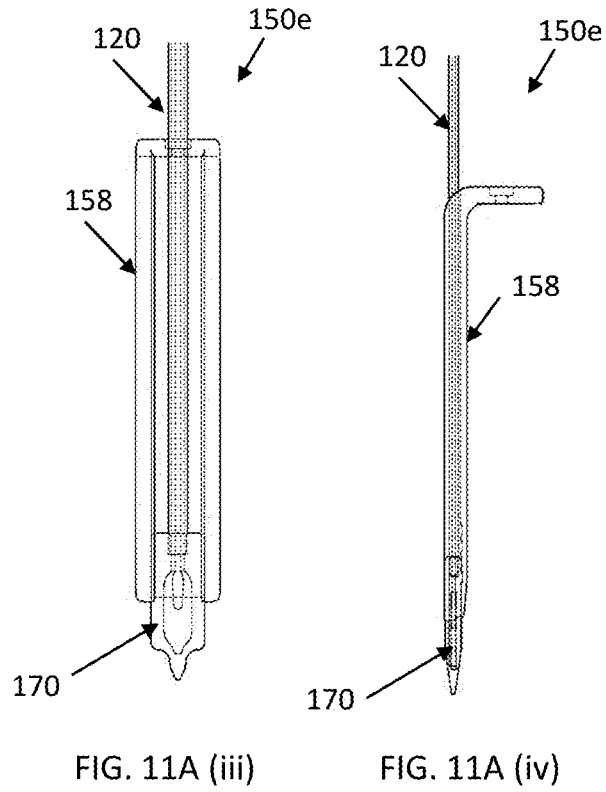
FIG. 11A (iii)          FIG. 11A (iv)

COOLING SYSTEMS, DEVICES, AND RELATED METHODS

CROSS REFERENCE TO RELATED APPLICATION

This application is a Continuation-In-Part (CIP) of and claims priority to International Application Number PCT/US2020/022974, filed 16 Mar. 2020, which claims priority to U.S. Provisional Application Ser. No. 62/818,921, filed Mar. 15, 2019, the contents of which are incorporated by reference herein.

BACKGROUND

Cooling devices present numerous benefits in the field of patient care. For example, the application of certain degrees of hypothermia to a patient's spine and spinal cord after a spinal cord injury can lead to benefits, such as a reduction of the metabolic demand of spinal cord cells, reduction of edema, added tolerance to hypoxia/ischemia, and ultimately a reduction in spinal cord tissue damage or cell death. Realizing these benefits could result in reduced neurologic damage or reduced tissue trauma. The use of a cooling effect for these purposes can be referred to as therapeutic hypothermia. Numerous other uses for therapeutic hypothermia exist and provide important benefits to patients, including application to brain and other neural tissue, muscle tissue and other organs.

SUMMARY

The disclosed systems and techniques can overcome issues with previously used techniques. Specifically, previous methods for cooling the spine (or other anatomical features of a patient) involve systemic cooling of the entire body. Such treatments carry a number of disadvantages. For example, systemic cooling techniques lack the ability to specifically target the injured tissue and, as a result, other unrelated tissue can be affected by the cooling with a wide variety of side effects. Systemic cooling also requires many hours to reduce the entire body by 5° C., as compared to local cooling which requires less than 30 minutes to reduce the local tissue by as much as 20° C. without affecting systemic body temperature. Any delay in administration of a therapeutic cooling effect to injured tissue is undesirable and likewise contraindicated in many clinical scenarios.

In some instances, it can be desirable to apply localized therapeutic hyperthermia to a patient. There is thus a continual need for improved methods and devices for applying thermal therapy to patients. Also, it is advantageous for systems that provide localized thermal treatment to a patient to be easy and safe for use in a clinical setting. In particular, systems for providing localized cooling that can be used in a sterile surgical environment and seamlessly integrate with current techniques are needed. The presently disclosed cooling systems and devices (e.g., retractor blades, retractor sheaths, and other devices) allow localized thermal therapy to be delivered in novel ways that can improve patient outcomes in a variety of clinical applications.

As discussed in more detail below, cooling systems are described herein that may be used in connection with one or more attached devices to cool patient tissue. The disclosed cooling systems can, and in some embodiments do, include a refrigeration unit containing a thermoelectric element in thermal communication with a heat exchanger, a fluid pump in fluid communication with a fluid inlet and a fluid outlet, tubing connecting the fluid inlet to the fluid outlet, a fluid cooling element in thermal contact with the thermoelectric element, and a temperature sensor positioned to detect a temperature of fluid within the tubing. The temperature of fluid within the tubing can be controlled by a control unit having a user interface and a power controller to adjust cooling power to the thermoelectric element. Various types of devices can be configured to receive and circulate cooled fluid from the cooling systems, such as retractor blades, cooling pads, scopes, and sheaths.

BRIEF DESCRIPTION OF THE DRAWINGS

FIG. 1A illustrates a first view of the self-contained cooling system, and FIG. 1B illustrates a second view of the self-contained cooling system shown in FIG. 1A.

FIG. 2A illustrates a general system architecture of the refrigeration unit and the control unit and their interaction and supply to a patient cooling device, while FIG. 2B illustrates particular features of the refrigeration unit and control unit in perspective view with the housing lids removed, and FIG. 2C shows a perspective view with the housings in place and a user interface shown.

FIGS. 2H(i) and 2H(ii) illustrate an exemplary control unit. In particular, FIG. 2H(i) illustrates a first view of the exemplary control unit and FIG. 2H(ii) illustrates a second view of the exemplary control unit shown in FIG. 2H(i).

FIG. 2I(i) illustrates a perspective view of an exemplary refrigeration unit.

FIG. 2I(ii) illustrates an isolated view of an exemplary refrigeration unit user interface.

FIGS. 2J(i)-2J(iv) illustrate an exemplary cooling system having a cooling element that is a plate. Specifically, FIG. 2J(i) shows a perspective view of a thermal assembly where the thermoelectric chip is located between the cooling element plate and an air heat exchanger. FIG. 2J(ii) shows a side view of FIG. 2J(i). FIG. 2J(iii) shows the cooling plate element with the overhead flow manifold removed to visualize internals of the cooling plate element. FIG. 2J(iv) shows the cooling plate, overhead flow manifold, thermoelectric chip and air heat exchanger in a see-through side-view.

FIGS. 2K(i)-2K(ii) illustrate an exemplary cooling system with a thermoelectric element and a cooling element that is encapsulated with foam. Specifically, FIG. 2K(i) shows a perspective view and FIG. 2K(ii) shows a side view of the exemplary cooling system.

FIGS. 2L(i)-2L(viii) illustrate an exemplary refrigeration unit without a housing to show an internal sub-frame configured in accordance with embodiments of the subject disclosure. Specifically, FIG. 2L(i) shows only the internal sub-frame, FIG. 2L(ii) shows the sub-frame with the thermal assembly, sensors, fan, and fluid pump, FIG. 2L(iii) shows the sub-frame with the thermal assembly, sensors, fan, fluid pump and a printed circuit board (PCB), and FIG. 2L(iv) shows a rear view of FIG. 2L(iii). FIG. 2L(v) shows the underside of the refrigeration unit with housing, fan, fan filter, and underside of sub-frame. FIG. 2L(vi) shows the refrigeration unit without a housing to illustrate the physical material separation between the internal sub-frame and exterior contact surfaces that thermally decouples the thermal assembly from the bottom of the sub-frame. FIG. 2L(vii) and FIG. 2L (viii) show left and right side views of the refrigeration unit without a housing, with exemplary fluid tubing connecting a pump to sensors to a cooling element and exiting housing, and signal cable connected to PCB exiting housing.

FIG. 2M (ii) shows an isolated view of the temperature sensor Tee fitting assembly, FIG. 2M (iii) shows a side view of one sensor placed in fluid communication with the thermal assembly and fluid tubing attached, FIG. 2M (iv) shows the same view as FIG. 2M (iii) but with two sensor assemblies, pump and additional fluid tubing, FIG. 2M (v) shows a cross section view of the sensor assembly with the sensor outer sheath in-tact, FIG. 2M (vi) shows the same cross section view of the sensor assembly with the sensor outer housing also sectioned to show the temperature sensor inside of the sheath, and FIG. 2M (vii) shows a cross section view of the sensor and sensor sheath without the Tee fitting assembly.

FIG. 3A shows a schematic layout top view of the control unit that has multiple docking ports to accommodate multiple individual refrigeration units, FIG. 3B shows a perspective view of multichannel control unit housing, FIG. 3C shows a perspective view of multichannel control unit affixed to a rolling stand with one independent refrigeration unit, FIG. 3D shows an internal cross section view of the multichannel control unit showing display, control unit, control PCB, power supply, power inlet and filter and docking area, FIG. 3E shows a schematic layout top view of the control unit and user interface, where the user interface has markings corresponding visually to the physical docking stations above.

FIGS. 5A (i)-5A (iii), FIGS. 5B (i)-5B (iii) and FIGS. 5C (i)-5C (v) illustrate an exemplary patient cooling device formed of two malleable material pieces with internal fluid conduits to allow fluid circulation from the cooling system to cool the malleable material. Specifically, FIG. 5A (i) shows a solid top view of a malleable tissue cooling device with fluid tubing and additional rigid mount for attachment to a surgical mount system, FIG. 5A (ii) shows a side view of the same as FIG. 5A (i), and FIG. 5A (iii) shows a perspective view of the same as FIG. 5A (i). FIG. 5B (i) shows a top view of the device with two additional rigid stiffening elements disposed inside of the fluid conduits and supported by unique structures above and below the malleable stiffeners, FIG. 5B (ii) shows the same as 5B (i) but without both stiffeners, and FIG. 5B (iii) shows the same cooling device in perspective view with only one malleable stiffener.

FIGS. 6A (i)-6A (ii) illustrate an exemplary patient cooling device formed of a malleable patient cooling device, or pad, adhered to the flat side of a rigid or malleable patient tissue retractor blade. FIG. 6A (i) shows a solid front view of a malleable tissue cooling device adhered to a rigid or malleable retractor blade with fluid tubing extending from the cooling device and FIG. 6A (ii) shows a solid side view of a malleable tissue cooling device adhered to a rigid or malleable retractor blade with fluid tubing extending from the cooling device.

FIGS. 7A (i)-7A (iv) illustrate an exemplary method of assembling a patient cooling device and novel delivery sheath, where the cooling device is placed inside of the sheath that has a closed end for insertion through an incision in patient tissue. FIG. 7A (i) shows a solid side view of a malleable tissue cooling device with fluid tubing extending from it being positioned to be inserted into the delivery sheath, FIG. 7A (ii) shows a transparent side view of a malleable tissue cooling device with fluid tubing extending from it positioned inside of the delivery sheath, FIG. 7A (iii) shows a transparent side view of the sheath only with additional texturing features and closed distal end, and FIG. 7A (iv) shows a solid perspective view of the sheath only with additional texturing features and closed distal end.

FIG. 8A (i) shows a solid front view of a cooling device assembly comprised of cooled malleable sheath over a rigid or malleable retractor blade with fluid tubing extending from the cooled sheath, FIG. 8A (ii) shows a solid side view of a cooling device assembly comprised of cooled malleable sheath over a rigid or malleable retractor blade with fluid tubing extending from the cooled sheath, FIG. 8A (iii) shows a solid perspective view of a cooling device assembly comprised of cooled malleable sheath over a rigid or malleable retractor blade with fluid tubing extending from the cooled sheath, FIG. 8A (iv) shows a solid perspective view of only the cooled sheath, and FIG. 8A (v) shows a solid perspective view of only rigid or malleable retractor blade.

FIGS. 8B (i)-8B (ii) illustrate an exemplary method of assembling a patient cooling device using a rigid or malleable retractor blade and novel cooling sheath. FIG. 8B (i) shows a solid side view of a cooling device assembly comprised of cooled malleable sheath and secondary blade receiving plug, over a rigid or malleable retractor blade with fluid tubing extending from the cooled sheath, FIG. 8A (ii) shows a perspective view of the same as FIG. 8B (i).

FIGS. 9A (i)-9A (vii) illustrate an exemplary method of assembling a patient cooling device using a rigid, flexible or malleable patient surgical scope and novel cooling sheath, where a fully contained malleable cooling sheath is placed over the scope. FIG. 9A (i) shows a solid side view of a cooling device assembly comprised of cooled malleable sheath with open end and over a rigid, malleable, or flexible surgical scope, with fluid tubing extending from the cooled sheath, FIG. 9A (ii) shows a transparent side view of the same assembly as FIG. 9A (i), FIG. 9A (iii) shows a transparent side view of the cooling pad sheath with a conical distal end for insertion through tissue, FIG. 9A (iv) shows a solid side view of the same assembly with a split open flat design that is wrapped around the scope and secured with a self-adhering strap, FIG. 9A (v) shows a solid perspective view of the same assembly as in FIG. 9A (iv), FIG. 9A (vi) shows a solid side view of the same assembly with temperature sensor disposed inside the cooling device reservoir, FIG. 9A (vii) shows a front solid view of an unfolded cooling sheath with serpentine fluid path.

FIGS. 10A (i)-10A (iii) illustrate an exemplary patient cooling device assembly with over-molded cap assembly, optional malleable stiffening elements, fluid tubing and coupler to cooling system. FIG. 10A (i) shows a perspective solid view of the entire cooling device assembly including between 1 and 10 feet of fluid tubing, with the patient contact side on the right side and coupler to cooling system on the left side, where the coupler assembly includes a mechanism to auto-lock the coupler once connected to the cooling system as well as features to allow blind and reversible connection, FIG. 10A (ii) shows a solid top-plane cut-away top view of the patient contact portion of the cooling device assembly illustrating the internal layout and assembly including a formed tubing in a U turn shape inserted into both outer lumens which carry return and supply cooled fluid from the cooling system, where the U turn has a relatively high melting temperature that allows over-molding of the cap as shown, and two optional malleable stiffeners occupy one or more of the center lumens, and FIG. 10A (iii) shows a solid transparent top view of the patient contact portion of the cooling device assembly described in FIG. 10A (ii).

FIGS. 10B (i)-10B (iii) illustrate an exemplary patient cooling device assembly with alternate cap assembly, lumen support tubing which may have partial or complete cutaways on the interior surfaces facing the reservoir, optional malleable stiffening elements, fluid tubing, and coupler to cooling system. Specifically, FIG. 10B (i) shows a perspective solid view of the entire cooling device assembly including between 1 and 10 feet of fluid tubing, with the patient contact side on the right side and coupler to cooling system on the left side, where the coupler assembly includes a mechanism to auto-lock the coupler once connected to the cooling system as well as features to allow blind and reversible connection, FIG. 10B (ii) shows a solid perspective view of the patient contact portion of the cooling device assembly illustrating where the cap is inserted into and permanently adhered or welded to the end of the extrusion to create closed-loop fluid flow between the cooling device and cooling system, FIG. 10B (iii) shows a transparent perspective view where the separate rigid or malleable cap is a second piece that is attached and welded or sealed around the perimeter of the joint between the cap and the tubing and where there are two formed tubing pieces with higher melting temperature where the tubing pieces are between 220 and 330 degrees and between 120 and 30 degrees of at least partially open wall that faces the interior reservoir on each side of the fluid lumen, FIG. 10B (iv) shows a perspective solid view of both formed tubing pieces in free air as they would be positioned in the assembly, FIG. 10B (v) shows a perspective solid top-plane cut-away view of the fluid tubing and secondary cap, FIG. 10B (vi) shows a perspective solid top-plane cut-away view of the fluid tubing and secondary cap where the optional stiffeners and outer formed tubing are shown in full form, and FIG. 10B (vii) shows a perspective solid top-plane cut-away view of the fluid tubing and secondary cap where the optional stiffeners and alternate outer formed tubing are shown in full form.

FIG. 11A (i)-(iv) illustrate an exemplary patient cooling device assembly that is comprised of a rigid retractor blade shim insert with internal reservoir and fluid tubing extending from shim A non-cooled traditional retractor blade with corresponding slots is used to retract tissue during surgery, and shims of different sizes shapes and functions are placed down the retractor blade slot and locked in place or otherwise loose. The cooled shim cools tissue that it contacts as well as the retractor blade which in turn cools additional patient tissue. Specifically, FIG. 11A (i) shows a perspective solid view of a cooled shim with a pointed end that has been inserted down a traditional slotted tissue retractor blade and fluid tubing extends from the shim, FIG. 11A (ii) shows a perspective transparent view of the same as FIG. 11A (i), FIG. 11A (iii) shows a front transparent view of the same as FIG. 11A (i), and FIG. 11A (iv) shows a side transparent view of the same as FIG. 11A (i).

It should be appreciated that features illustrated in the accompanying figures may not necessarily be drawn to scale and that the geometry depicted in the figures can vary from the images shown. Alternative arrangements and adjustments of componentry shown may be within the reach of one skilled in the art and the figures of the subject application are not meant to limit the disclosure to the particular embodiments depicted.

DETAILED DESCRIPTION

Figure 1A:
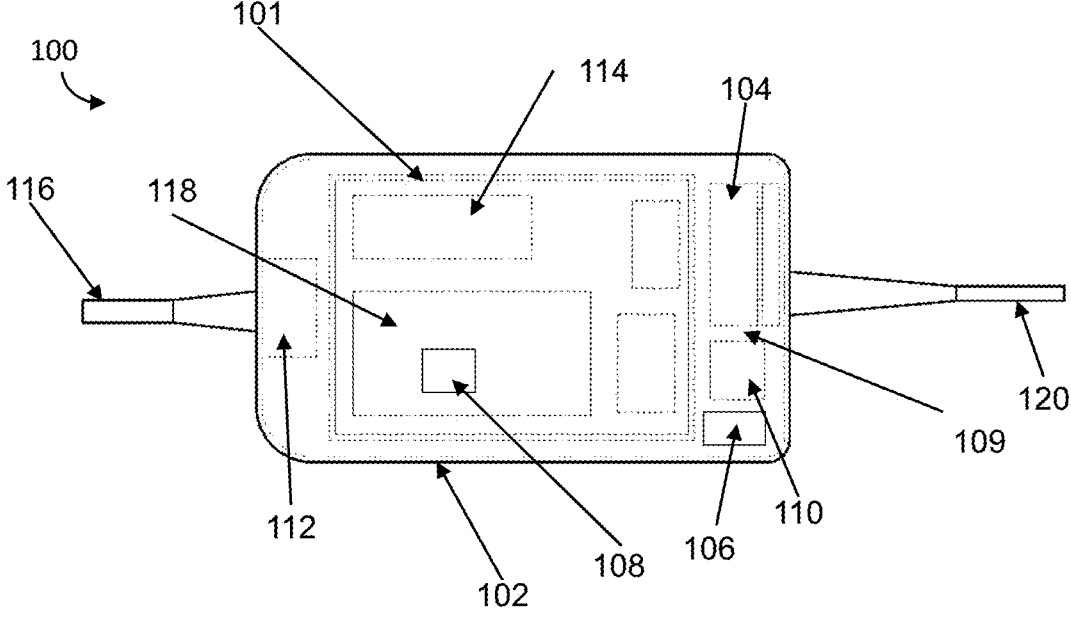
FIGS. 1A-1B show perspective views of an exemplary self-contained cooling system configured having combined refrigeration and control unit components, in accordance with some embodiments of the subject disclosure. Specifically.
Figure 1B:
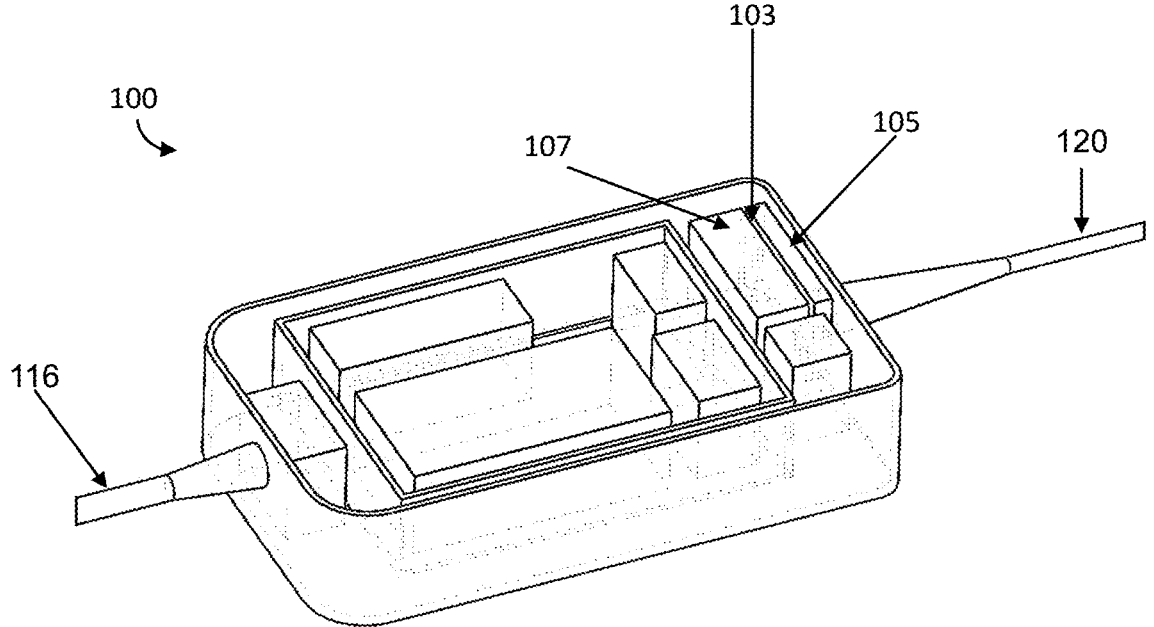
Figure 2A:
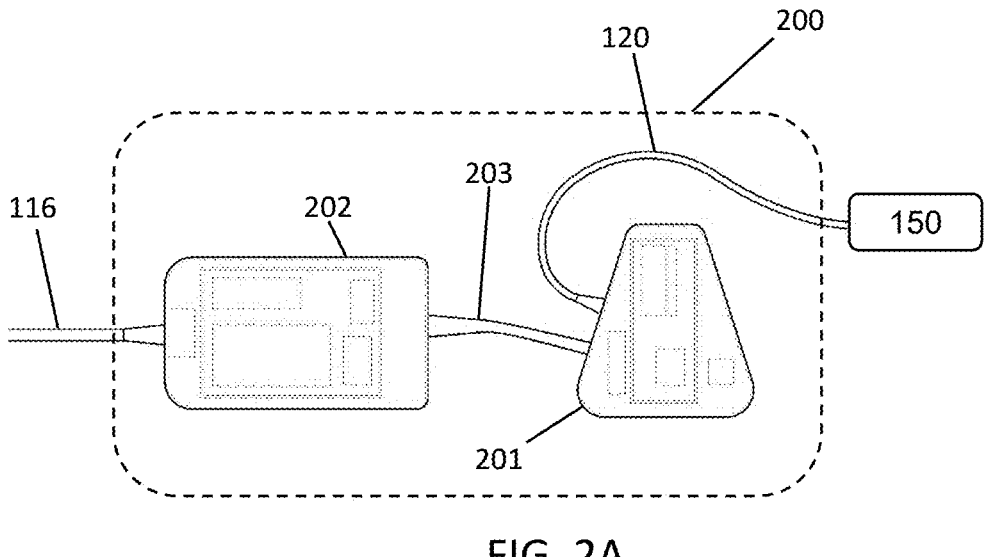
FIGS. 2A-2C illustrate perspective view of exemplary cooling system having distinct refrigeration unit and control unit components, configured in accordance with some embodiments of the subject disclosure.
Figure 2B:
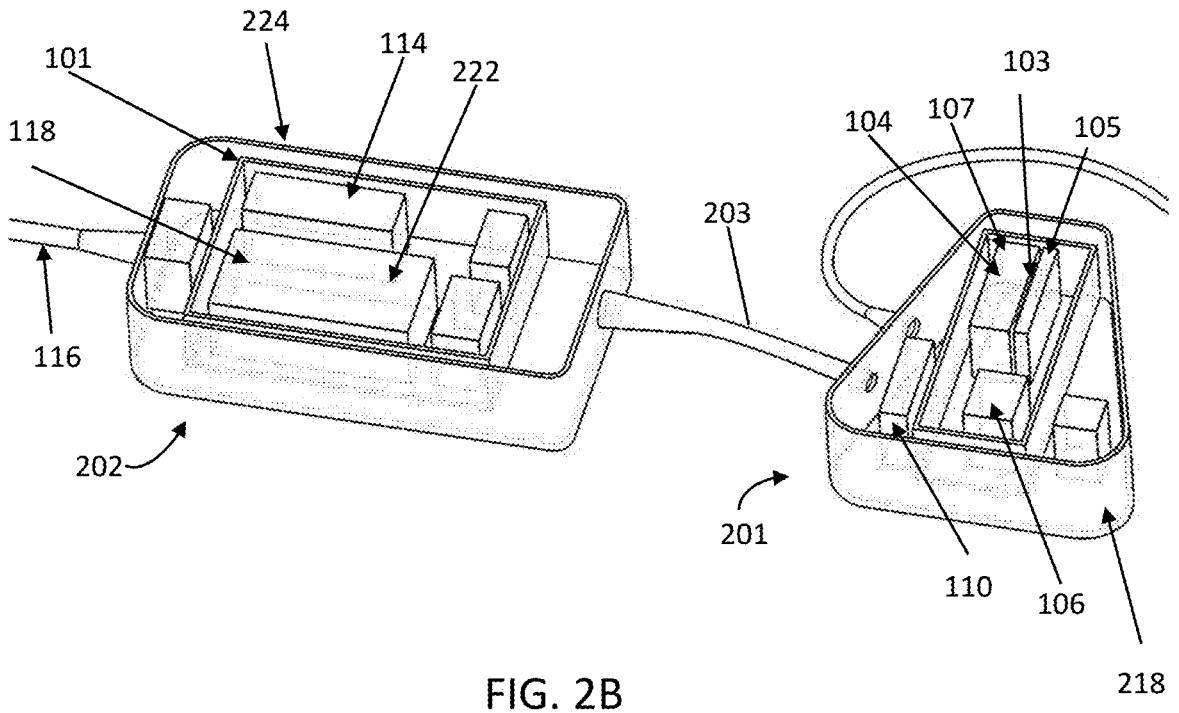
Figure 2C:
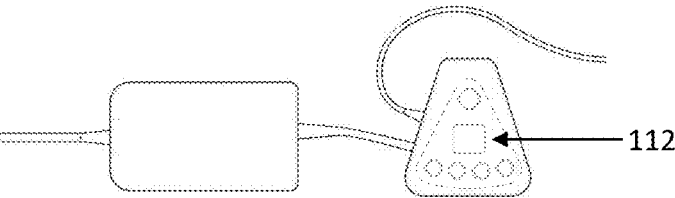

Cooling systems, namely systems for providing targeted cooled fluids for cooling anatomical features of a patient, are disclosed herein. The disclosed cooling systems can be self-contained or may be formed of distinct components that can be linked together to form a complete cooling system. The disclosed cooling systems can include various features, such as but not limited to: pumps, fans, heat exchangers, reservoirs, fluid, sensors, controllers, power management, compressors and/or thermoelectric chips. The disclosed cooling can be used to cool fluid that is exported via a fluid tube and delivered to a device that is placed in contact with patient tissue. Numerous types of devices capable of receiving the cooled fluid exported from the disclosed cooling systems are described herein, such as but not limited to tissue retractor blades, malleable devices, and sheaths. As discussed in further detail in the following sections, the disclosed cooling systems connect to fluid tubing exiting the housing of the refrigeration unit and completes the closed-circuit flow of temperature-controlled fluid, circulating between the refrigeration unit and the cooling device at the patient. In this way, the disclosed systems provide localized thermal therapy to a patient. It is understood that internal hardware, mounts, ties, electrical cable, and fluid cabling (not shown in figures) are implied as included in all embodiments, to assemble and connect components internal to the housing as applicable. The disclosed cooling systems are configured to facilitate clinical use and ensure sterility. In some embodiments, the cooling system includes separate components, whereas in other embodiments, the cooling system is integrated within a single housing. FIGS. 1A-1B illustrate an embodiment in which the cooling system is integrated within a single housing and FIGS. 2A-2C illustrate an embodiment in which the cooling system includes distinct components. It is to be understood that some features discussed with respect to the first exemplary cooling system 200 shown in FIGS. 2A-2C are common to the second exemplary cooling system 100 shown in FIGS. 1A-1B. Accordingly, common reference numerals and/or descriptions are used herein to describe features of first exemplary cooling system 200 and/or second exemplary cooling system 100.

The presently disclosed cooling systems can be configured to deliver cooling to a single fluid tubing or to multiple fluid tubing. The cooling systems are unique in their minimal size and adaptability to clinical environments. Various types of cooling systems, devices, and methods of use are described in detail in the following sections.

First Exemplary Cooling System

FIGS. 2A-2C illustrate an exemplary cooling system 200 having a refrigeration unit 201 and a control unit 202. The refrigeration unit 201 may be electrically connected to the control unit 202 via a signal cable 203, as illustrated in FIGS. 2A-2C. As shown in FIG. 2B, components of the refrigeration unit 201 and control unit 202 may each be contained within a housing. Particular features of refrigeration unit 201, control unit 202, and signal cable 203 are discussed below in detail.

The refrigeration unit 201 may include a thermoelectric element 103 (for example, a thermoelectric chip) in thermal communication with a heat exchanger 107. In these and other embodiments, refrigeration unit 201 may also include a fluid pump 106 in fluid communication with a fluid inlet and a fluid outlet. A fluid cooling element 105 may also be present within refrigeration unit 201. If present, fluid cooling element 105 may be in thermal contact with the thermoelectric element 103. If desired, refrigeration unit 201 may also include a fan 110, internal tubing, and/or a fluid connector that is engageable with a patient cooling device (discussed in a following section). In particular, the fluid connector may be configured to provide (cooled) fluid from the tubing to a patient cooling device. As shown in FIG. 2B, refrigeration unit 201 may include a thermal assembly 104 and a printed circuit board. Refrigeration unit 201 may also include a temperature sensor, a power signal connector, and/or a user interface, if desired. Various componentry of the refrigeration unit 201 may be mounted on a sub frame. FIG. 2B illustrates that a housing 218 may contain all internal features of refrigeration unit 201.

As shown in FIG. 2B, the control unit 202 can include a power cable 116 (alternatively referred to as a 'power connector' herein), a power inlet, a power controller 222, and/or a power switch. In some embodiments, the power inlet includes a power filter. In these and other embodiments, the power controller 222 includes a printed circuit board 118. As will be appreciated by those skilled in the art upon consideration of the subject disclosure, the power controller 222 can be used to adjust cooling power to the thermoelectric element 103. Control unit 202 may, in some embodiments, include a power supply 114. As shown in FIG. 2B, internal componentry of control unit 202 may be contained within a housing 224.

FIG. 2C illustrates features of an exemplary refrigeration unit 201 and an exemplary control unit 202 of cooling system 200 shown in FIGS. 2A and 2B. It will be appreciated that in some embodiments, signal cable 203 may carry signals from temperature sensors and user interface 112 from refrigeration unit 201 to control unit 202. Control unit 202 can be configured to process system state, signals, and/or user commands and signal cable 203 may modulate power signals from control unit 202 to refrigeration unit 201.

Figure 2D:
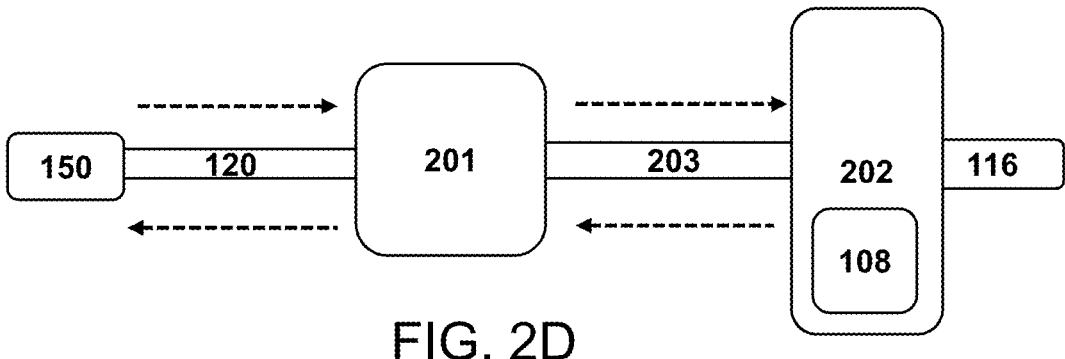
FIG. 2D illustrates functionality and arrangement of an example refrigeration unit, control unit, and patient cooling device, in accordance with various embodiments of the subject disclosure.

FIG. 2D shows a diagram illustrating the flow of fluids between refrigeration unit 201 and sub frame and the signal exchanges between refrigeration unit 201 and control unit 202. FIG. 2D shows the entire cooling system 200, including the control unit 202 that receives power from an AC power source via the power cable 116.

Figure 2E:
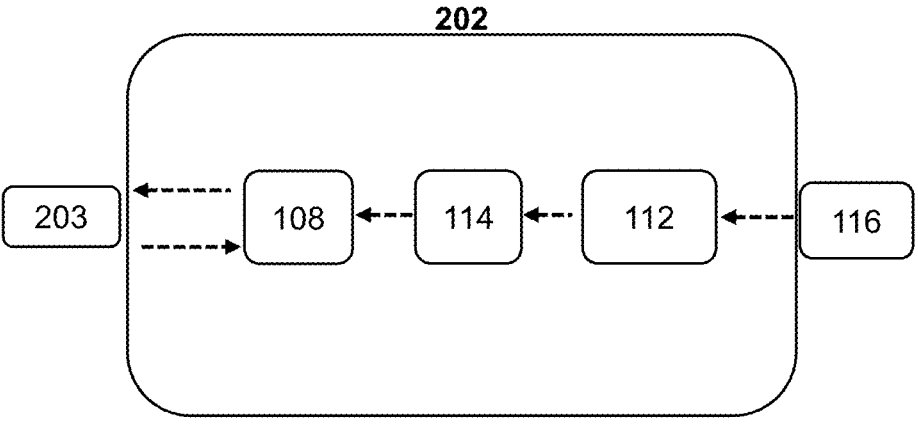
FIG. 2E illustrates functionality and arrangement of an example control unit.

FIG. 2E shows a diagram of control unit 202, signal cable 203, and power cable 116.

Figure 2F:
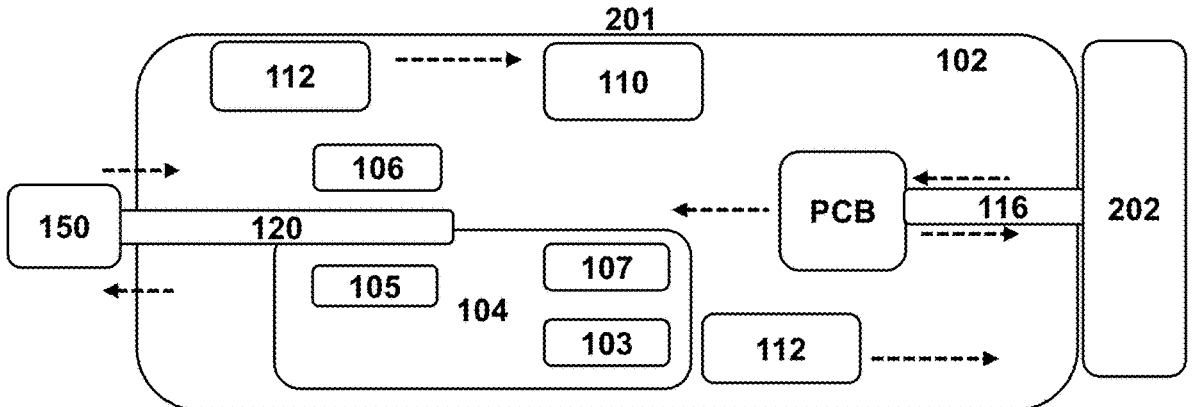
FIG. 2F illustrates functionality and arrangement of an example refrigeration unit relative to a patient cooling device and control unit.

FIG. 2F shows a diagram of refrigeration unit 201, power cable 116, and fluid cable 120.

Second Exemplary Cooling System

FIGS. 1A-1B illustrate an exemplary self-contained cooling system 100 (at times referred to herein as "cooling system" or "cooling system 100"). As shown in FIG. 1A, the self-contained cooling system 100 includes a housing 102 that contains various components, including a thermal assembly 104, a pump 106, a control processor 108, and a fan 110. Housing 102 also may include a power inlet 112, as shown in FIG. 1A. If desired, power inlet 112 may include a filter to reduce electromagnetic interference. Power inlet 112 is permanently or detachably connected to a power cable 116, as shown in FIG. 1A. In some embodiments, power inlet 114 may be in electrical communication with a power supply 114. As will be appreciated by those skilled in the art, power supply 114 may be configured to convert and/or store electrical energy. Power supply 114 may be configured for alternating current (AC) and/or direct current (DC). Power supply 114 may be configured to provide power with two means of patient protection (MOPP). Power supply 114 may connect to control processor 108 which regulates power to fan 110, pump 106, cooling unit inside of thermal assembly 104.

The thermal assembly 104 may contain a fluid cooling element, such as a thermoelectric chip, liquid heat exchanger and/or an air heat exchanger, in some embodiments. Pump 106 may be connected to thermal assembly 104 to provide fluid flow into thermal assembly 104 during operation to cool the fluid circulated through the cooling system 100. In some embodiments pump 106 may be connected to the fluid cable 120 entering or exiting the housing 102. Thermal assembly 104 may be connected to the fluid cable 120 entering or exiting the housing 102. In some embodiments, one or more temperature sensors 111 may be placed in or near the fluid to measure the fluid temperature. It should be appreciated that temperature sensors 111, if present, may be submerged within the fluid or be positioned external to the fluid.

Housing 102 may include a user interface 112 to allow easy operation of the power state, operation mode, and selected temperature. If desired, housing 102 may include electrical shielding coating on the interior surface. Housing 102 may be comprised of one or more modular shells 109 that are permanently attached to create a singular housing.

As shown in FIG. 1A, a fluid cable 120 extends through the housing 102 and is coupled to fluid tubing that connects it to a thermal assembly 104, sensors 111, and pump 106. Cooling system 100 may include a thermoelectric element 103, such as a thermoelectric chip, in thermal communication with a heat exchanger 107. In select embodiments, heat exchanger 107 may be an air heat exchanger or other type of heat exchanger. Fluid pump 106 may be in fluid communication with a fluid inlet and a fluid outlet. A fluid cooling element 105 may be in thermal contact with thermoelectric element 103. Cooling system 100 may also include a fan 110, as shown in FIG. 1A. Control processor 108 can be configured to adjust power provided to the thermoelectric element 103 to increase or decrease cooling of the fluid.

In some embodiments, housing 102 may include one or more sub-frames 101 to support various internal components of the self-contained cooling system 100, as shown in FIG. 1A. Additionally, in select embodiments, the self-contained cooling system 100 may optionally include a printed circuit board 118 (which may also be referred to as a "PCB"). Printed circuit board 118 may be separate or integral to the control processor 108, in some embodiments.

Subframe 101, if present, may have a singular or modular structure that supports internal components that are not affixed directly to the housing. The subframe 101 may be metal or plastic, and may be welded or otherwise fused, in some embodiments. In select embodiments, subframe 101 may be assembled with snaps, screws, rivets, adhesive, or similar fasteners. The subframe 101 may support the pump, fan, thermal assembly, sensor, tubing, or other componentry, as desired.

Cooling System Attached to Patient Cooling Device

Figure 2G:
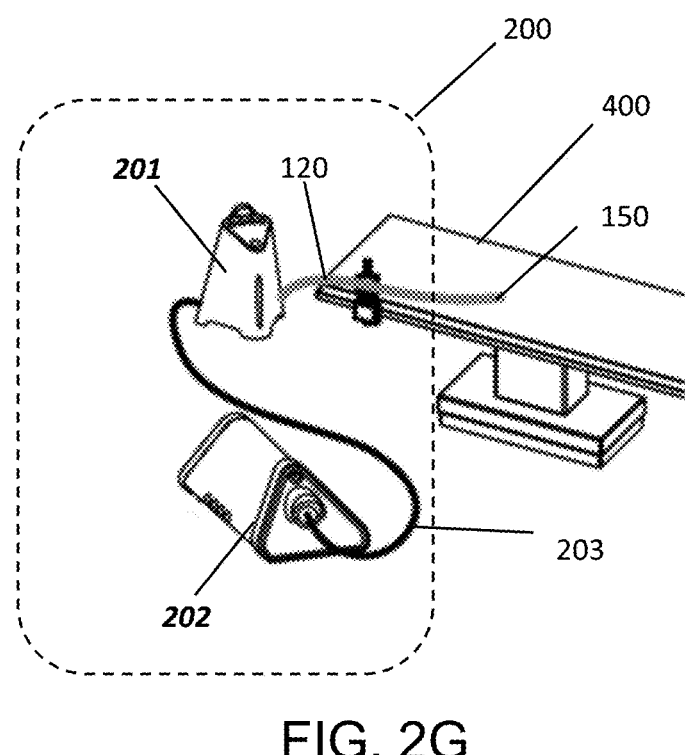
FIG. 2G illustrates an exemplary cooling system connected to a patient cooling device relative to a patient bed.

The disclosed cooling systems may be used in connection with one or more patient cooling devices to deliver thermal therapy to a patient. For example, FIG. 2G illustrates an exemplary cooling system 200 connected to a patient cooling device 300. As shown in FIG. 2G, the refrigeration unit 201 is connected to control unit 202 via signal cable 203. Fluid cable 120 that is cooled by refrigeration unit 201 is in fluid communication with a patient cooling device 300. The patient cooling device 150 may be secured to a table 400 with a fastener, such as a clip, clamp, or other device. Although one particular placement is illustrated in FIG. 2G, many other configurations are possible and contemplated herein. For example, in some embodiments, the refrigeration unit 201 may be placed on a table, hung from a stand, hung from a table-mounted stand, or otherwise placed in proximity to the patient. In select embodiments, a table-mounted stand may also securely retain signal cable 203 and/or a coupler that pairs the refrigeration unit 201 to a patient cooling device 150. Particular patient cooling devices 150 are discussed in detail in a later section.

FIGS. 2H(i) and 2H(ii) illustrate an exemplary control unit 202. In particular, FIG. 2H(i) illustrates a first view of the exemplary control unit 202 and FIG. 2H(ii) illustrates a second view of the exemplary control unit 202 of FIG. 2H(i).

FIGS. 2I(i) and 2I(ii) illustrate an exemplary refrigeration unit 201. In particular, FIG. 2I(i) illustrates a first view of the exemplary refrigeration unit 201 and FIG. 2I(ii) illustrates a second view of the exemplary refrigeration unit 201 shown in FIG. 2I(i). As shown in FIG. 2I(ii), refrigeration unit 201 may include a user interface 112, in some embodiments.

Optional Cooling System Features

The following optional cooling system features could be implemented with the first exemplary cooling system 202 and/or the second exemplary cooling system 100 described herein. For ease of description, the general term 'cooling system' will be used, however, the term 'cooling system' as used herein should be understood to apply to one or both cooling system 100, cooling system 200 and also cooling system 300.

In some embodiments, the fluid cooling element 105 and of the cooling system is a plate. FIGS. 2J(i)-2J(iv) illustrate an exemplary cooling system having a cooling element 105 that is a plate. In some such embodiments, the plate cooling element 105 may be a thermally conductive metal with or without an electrically insulating coating.

In some embodiments, the thermoelectric element 103 may be encapsulated, such as, for example, with silicone. The fluid cooling element 105 and/or thermoelectric element 103 may be in contact with insulation, in some embodiments. In some such embodiments, the insulation may be closed cell foam. In these and other embodiments, five sides of the cooling element and the thermoelectric element may be surrounded by foam and the sixth side of the cooling element 105 may be in contact with the thermoelectric element. FIGS. 2K(i)-2K(ii) illustrate an exemplary cooling system 200 with a fluid cooling element 105 that is encapsulated with foam 226.

In some embodiments, the components of the disclosed cooling systems may be internally supported by a sub-frame 101. In some such embodiments, the sub-frame 101 may be formed of sheet metal or other suitable material. If present, the sub-frame 101 may thermally decouple the housing from the heatsink (see FIG. 2L(vi)). In these and other embodiments, an insulating material may be disposed between the heatsink and the housing and/or sub-frame 101.

FIGS. 2L(i)-2L(viii) illustrate an exemplary refrigeration unit 201. In particular, FIGS. 2L(i)-2L(viii) illustrate an exemplary refrigeration unit 201 without a housing (218) present to show an internal sub-frame 101 configured in accordance with embodiments of the subject disclosure. Specifically, FIG. 2L(i) shows only the internal sub-frame 101, FIG. 2L(ii) shows the sub-frame 101 with the thermal assembly 104, sensors 111, fan 110, and fluid pump 106, FIG. 2L(iii) shows the sub-frame 101 with the thermal assembly 104, sensors 111, fan 110, fluid pump 106, and PCB 118. FIG. 2L(iv) shows a rear view of FIG. 2L(iii). FIG. 2L(v) shows the underside of the refrigeration unit 201 with housing 218, fan 105, a fan filter, and underside of sub-frame 101. FIG. 2L(vi) shows the refrigeration unit 201 without housing 218 to illustrate the physical material separation between the internal sub-frame 101 and exterior contact surfaces that thermally decouples the thermal assembly 104 from the bottom of the sub-frame 101. FIG. 2L(vii) and FIG. 2L (viii) show left and right-side views of the refrigeration unit 201 without housing 218, with exemplary fluid tubing 122 connecting pump 106 to sensors 111 to cooling element 105 and exiting housing 218, and signal cable 203 connected to PCB 118 exiting housing 218.

It should be understood that fluid tubing 122 can accommodate any suitable type of fluid. For example, in some embodiments, the fluid circulated through tubing 122 (and consequently through the entire cooling system) may be either a liquid or a gas. In select embodiments, a sterile liquid fluid is used in the cooling system. It is to be understood that the terms 'tubing 122', 'fluid cable 120' and/or 'fluid tubing 120' may be used interchangeably herein. In particular, in some cases, 'tubing 122' is used to refer to internal tubing within the refrigeration unit 201 and 'fluid tubing 120' or 'fluid cable 120' is used to refer to either the same piece of tubing or tubing that is in fluid connection with tubing 122.

As will be appreciated upon consideration of the subject disclosure, various components of the refrigeration unit 201 may be in fluid communication. For example, in some embodiments, pump 106, temperature sensor(s) 111, fluid cooling element 105, a fluid inlet, and a fluid outlet may all be in fluid communication. Furthermore, the fluid path between these components may create an internal closed-loop flow within the refrigeration unit 201.

Any suitable type of temperature sensor device 111 may be used in connection with the disclosed cooling systems. For example, the temperature sensor(s) 111 present may, in some embodiments, include a thermistor probe disposed in a metal sheath. In some such embodiments, the metal sheath and probe assembly may be positioned inside a plastic fluid fitting. The plastic fluid fitting may be T-shaped in some embodiments. The probe feature of temperature sensor 111, if present, may be inserted into a first opening in the fitting such that fluid passes over the sensor 111 as fluid flows into the second opening and out of the third opening of the fitting. In some such embodiments, no fluid may pass through the first opening of the fitting. The fitting and probe assembly may be sealed using one or more layers of wrapping, which may be glued or bonded using heat. In some embodiments, the temperature sensor 111 and fitting assemblies may be positioned in the refrigeration unit housing 218 where sensor probe is angled above the horizontal plane (0°) at least 1 degree with the probe tip pointing upward, however, numerous other variations are possible and contemplated herein.

Figure 2M:
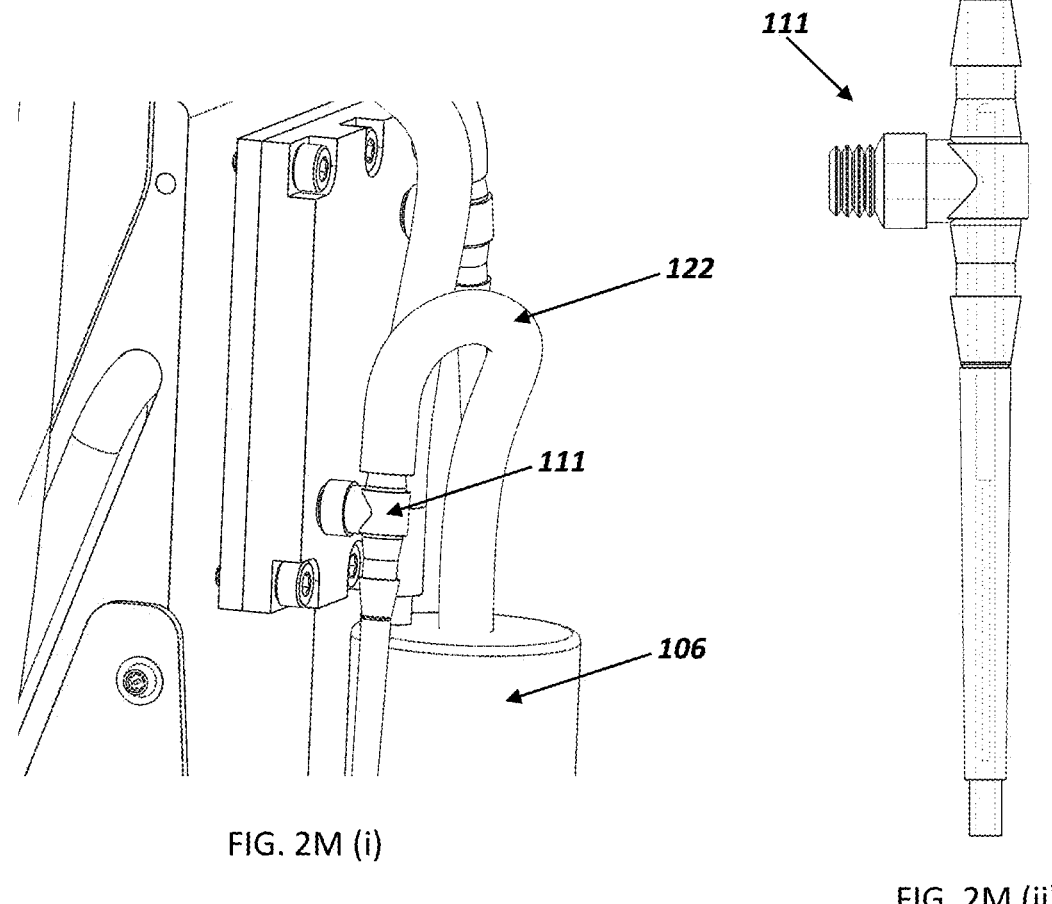
FIGS. 2M(i)-2M(vii) illustrate an exemplary refrigeration unit temperature sensor in partial cutaway and isolated views to show the sensor construction. Specifically, FIG. 2M (i) shows two sensors in Tee fitting assemblies mounted to the thermal assembly with fluid tubing connected.

FIGS. 2M(i)-2M(vii) illustrate an exemplary refrigeration unit temperature sensor 111 in partial cutaway and isolated views to show the sensor 111 construction. Specifically, FIG. 2M (i) shows two sensors in Tee fitting assemblies mounted to the thermal assembly 104 with fluid tubing 122 connected thereto. FIG. 2M (ii) shows an isolated view of the temperature sensor 111 Tee fitting assembly, FIG. 2M (iii) shows a side view of one sensor 111 placed in fluid communication with the thermal assembly 104 and fluid tubing 122 attached. FIG. 2M (iv) shows the same view as FIG. 2M (iii) but with two sensor assemblies 111a, 111b, pump 106, and two fluid tubings 122a, and 122b. FIG. 2M (v) shows a cross section view of the sensor assembly 111 with the sensor outer sheath in-tact, FIG. 2M (vi) shows the same cross section view of the sensor assembly 111 with the sensor outer housing also sectioned to show the temperature sensor 111 inside of the sheath, and FIG. 2M (vii) shows a cross section view of the sensor 111 and sensor sheath without the Tee fitting assembly.

It should be understood that printed circuit board 118 may be positioned inside or outside of the control unit housing 224 or housing 102, depending on whether cooling system 100 or cooling system 200 is used. In select embodiments, cooling system 200 may be configured to have the signal cable 203 exit the refrigeration unit through the bottom of housing 218 at an angle greater than 15°.

User interface 112 may be configured as desired. In some embodiments, user interface 112 may be configured to display temperature as measured by temperature sensor(s) 111. In some embodiments, temperature may be displayed on user interface 112 as a two-digit numeric form. The temperature displayed on user interface 112 may be equivalent to or nearly equivalent to the temperature of fluid within a patient cooling device 150 attached to the cooling system 100/200. Exemplary patient cooling devices 150 are discussed in a separate section but may be, for example, a retractor blade with internal fluid paths, a bone screw with internal fluid paths, or a tissue cooling pad with internal fluid paths.

The user interface 112 can be configured to provide a current status of the cooling system. For example, the user interface 112 can include one or more lights, which ca indicate a cooling state of the cooling system. The displayed cooling can be either a set temperature or a power level. The user interface 112 may optionally include one or more user input buttons which can be used to adjust the controller, and in turn the liquid cooling plate, to a desired temperature. It should be appreciated that any number of user interface elements may be used to select and/or adjust the temperature (e.g., buttons, dials, sliders, or other manually selectable features either in a physical medium or in a graphical user interface). In some embodiments, the user interface 112 can be configured to display one or more of the following: a measured temperature of fluid within the self-contained refrigeration unit, a temperature setting control, and/or a status indicator for the self-contained refrigeration unit. In some embodiments, the temperature setting control adjusts the thermoelectric element (for example, by changing the power supplied to the thermoelectric element). In other embodiments, however, the temperature setting control adjusts the flow rate of the fluid.

Power input to the cooling system 100/200/300 may be controlled by a processor, voltage feedback loop, or other componentry. If present, the processor may measure temperature(s) inside the refrigeration unit 201, inside of the fluid path, on or near a heat exchanger 107, or on or near the fluid cooling element 105. In some such embodiments, the processor may calculate the temperature of fluid flowing through fluid cable 120 to patient cooling device 150. The temperature of the fluid can be measured at one or more positions. For example, temperature sensors may be positioned at the liquid inlet, at the liquid outlet, and/or at a position between the liquid inlet and the liquid outlet.

The power supply connector may be fixedly connected to a self-contained refrigeration unit and/or the power filter, in some embodiments. In these and other embodiments, the power supply connector may include a 3-prong grounded AC plug.

Cooling system 100/200/300 may include a fan 110 positioned to pull air into or expel air out of housing(s) of the cooling system. In some embodiments, fan 110 may be an axial fan and may be positioned to direct air into or out from a bottom, side or top region(s) of the housing(s). In these and other embodiments, air may be pulled through an EMI filter prior to entering the fan 110. If present, the EMI filter may be a passive grate or may be formed of a plurality of holes or slots formed in the material and/or in a separate piece. In some embodiments, a bottom fan may include an EMI filter formed in an add-on piece and the air inlet material may include a patterned EMI integrally formed therein.

In some embodiments the cooling system may include a heat exchanger. In some embodiments, the heat exchanger is a passive air heat exchanger, and the self-contained refrigeration unit further comprises a liquid heat exchanger and air exiting the fan passes over one or more of the liquid heat exchanger and the passive air heat exchanger. In these and other embodiments, the cooling system may include a power filter, such as a dual stage power filter. In these and other embodiments, the leakage current after the power filter is less than 15 uA. The power filter may have a Capacitance (Cx) of between 100 and 300 nF and a resistance of between 500 and 1500 kOhm. The power filter may reside in a separate filter box inside the housing and a DC power line may connect the filter box to the power supply inside the housing.

Multi-Unit Console Cooling System

Figure 3A:
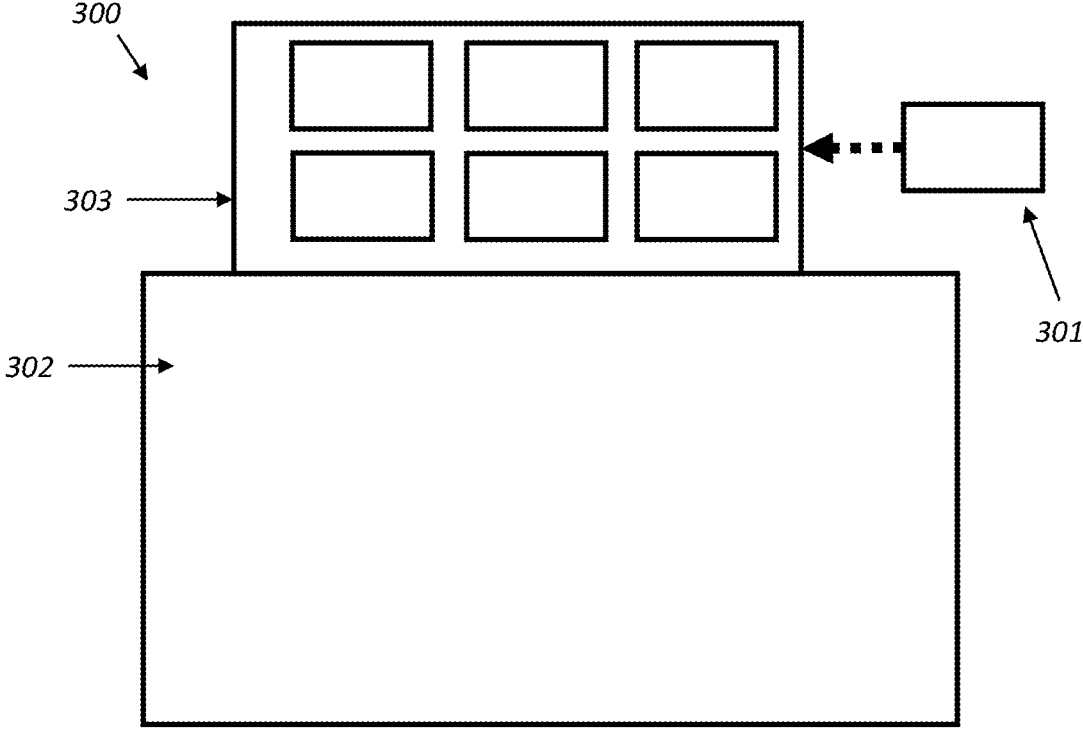
FIGS. 3A-3E illustrate an exemplary cooling system with independent refrigeration units and a multichannel control unit. Specifically.
Figure 3B:
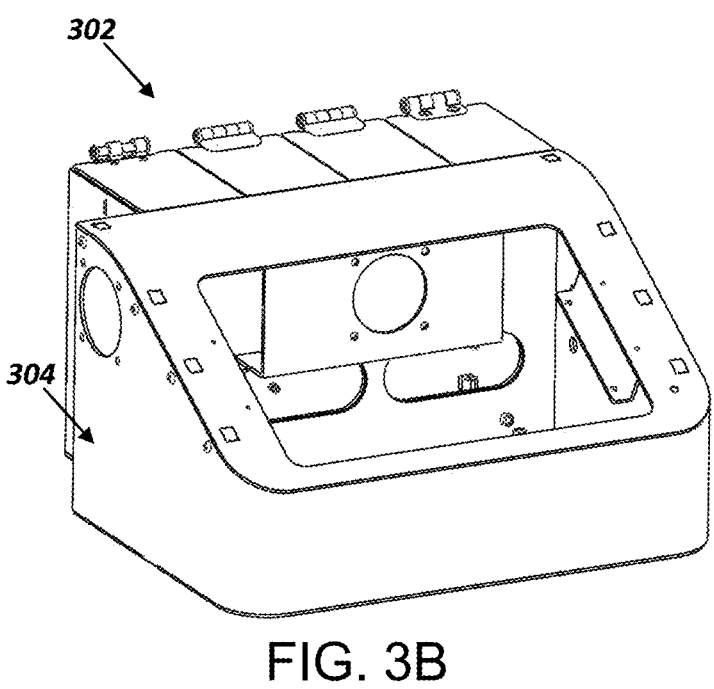
Figure 3C:
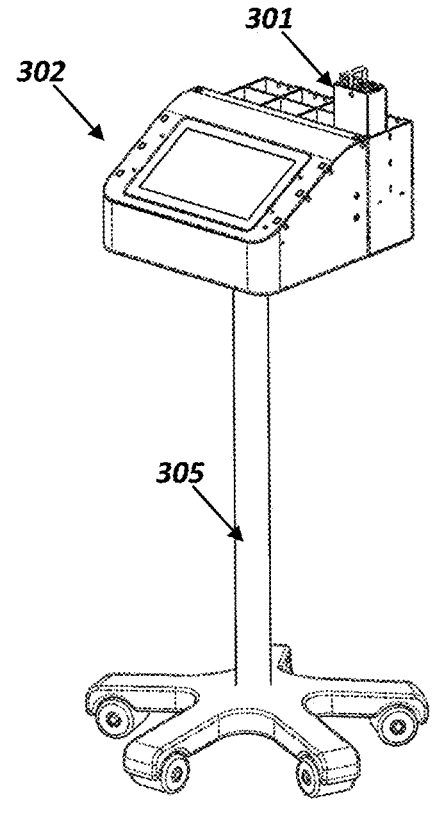
Figure 3D:
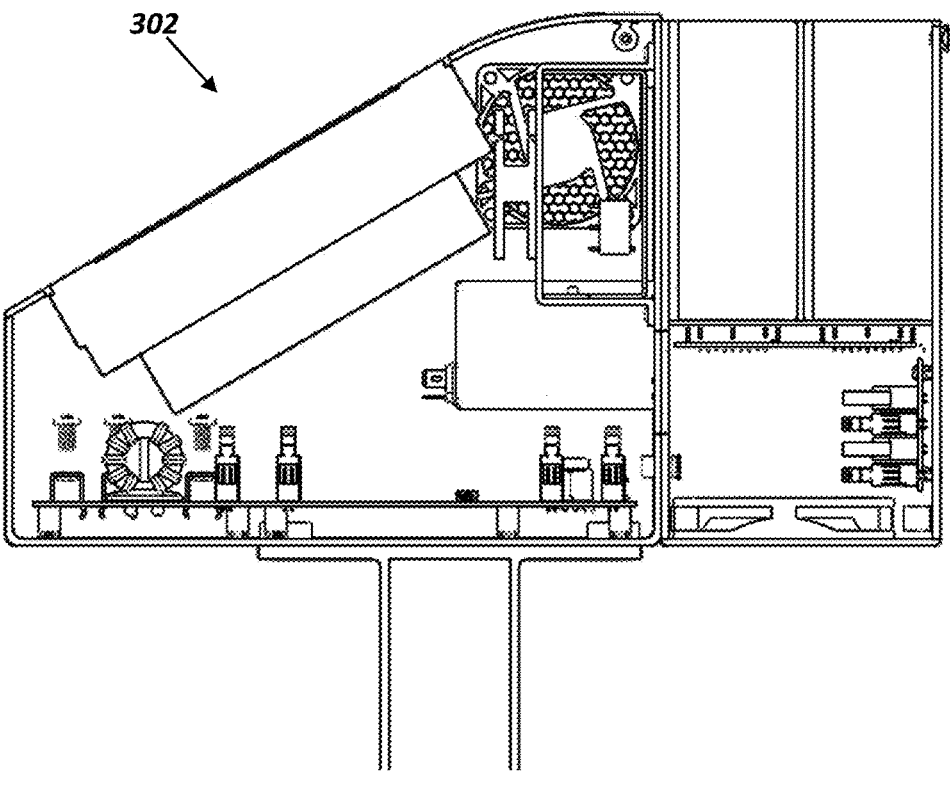
Figure 3E:
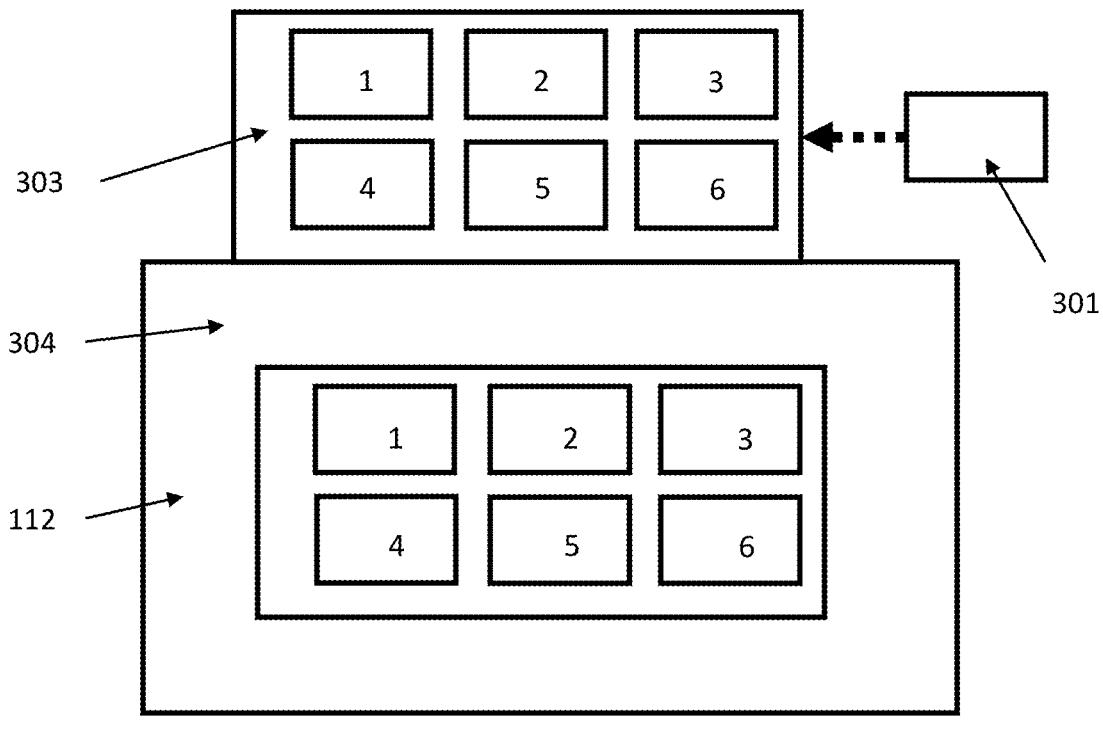

FIGS. 3A-3E illustrates an exemplary multi-unit console cooling system 300. In particular, FIGS. 3A-3E illustrate an exemplary cooling system 300 with independent refrigeration units 301 and a multichannel control unit 302. Specifically, FIG. 3A shows a schematic layout top view of the control unit 302 that has multiple docking ports in docking area 303 to accommodate multiple individual refrigeration units 301. FIG. 3B shows a perspective view of the housing 304 for multichannel control unit 302. FIG. 3C shows a perspective view of multichannel control unit 302 affixed to a rolling stand 305 with one independent refrigeration unit 301. FIG. 3D shows an internal cross section view of the multichannel control unit 302 showing a display, control unit, control PCB, power supply, power inlet and filter, and docking area. FIG. 3E shows a schematic layout top view of the control unit 302 and user interface 112, where the user interface 112 has markings corresponding visually to the physical docking stations present in the cooling system 300.

As shown in FIGS. 3A-3E, the multi-unit console cooling system 300 may include a plurality of powered cassette slots in a docking area 303, a plurality of cassettes (i.e., independent refrigeration units 301), each shaped to fit in a powered cassette slot. Each cassette can include a complete closed-loop circuit (as previously described herein with respect to cooling system 100/200). Cooling system 300 can, in some embodiments, be coupled to a patient cooling device 150, as discussed in a separate section herein. The temperature of each cassette can be controlled by a multichannel control unit 302. The multichannel control unit 302 can have any features discussed herein with respect to control unit 202 or controller processor 108.

In some embodiments, the powered cassette slots may be vertically oriented. The powered cassette slots may each comprise a multi-connection electrical interface and at least one open hole, in some embodiments. In some such embodiments, the at least one open hole may be covered with a metal mesh. Each cassette may be independently controlled by a controller, if desired. In some such embodiments, each cassette may have a temperature that is controlled independently from the other cassettes. In these and other embodiments, the closed-loop circulation of each cassette may be independent from the other cassettes.

In some embodiments, upon providing power to the control console 302, the plurality of cassettes each individually possess an initial power state comprising: a thermoelectric element, pump, fans all powered. In these and other embodiments, after ceasing operation, the plurality of cassettes each individually possess a completion power state that includes: maintaining the fan power at nominal voltage and turning off power to the thermoelectric element and pump. The user interface may be designed to match the physical layout and positioning of the individual refrigeration units docked above, as seen by the user.

Patient Cooling Devices

Figure 4A:
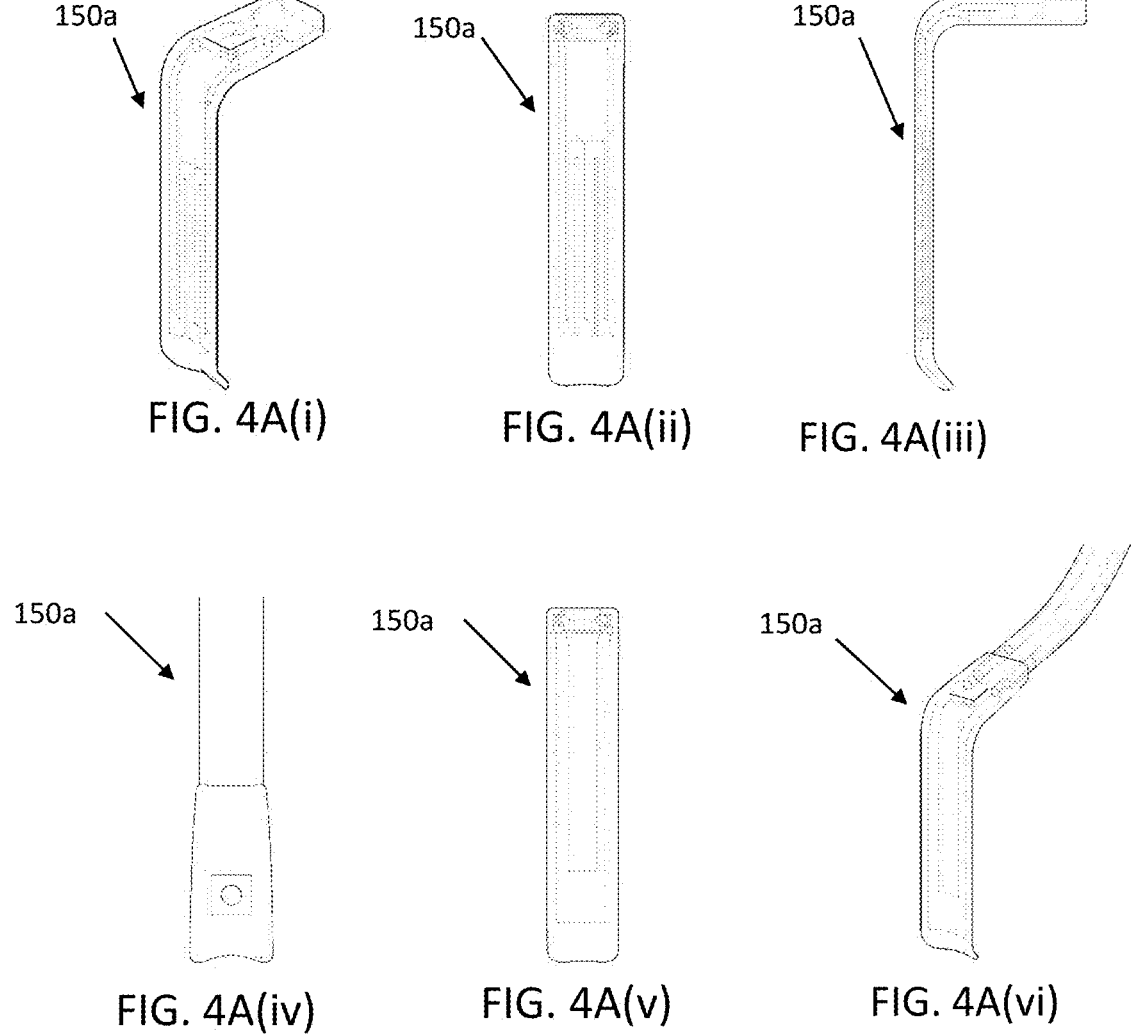
FIGS. 4A (i)-4A (vi) and FIGS. 4B (i)-4B (vi) illustrate an exemplary patient cooling device formed of a rigid material with internal fluid conduits to allow fluid circulation from an attached cooling system to cool the rigid material. Specifically, FIG. 4A (i) shows a perspective transparent view of a rigid tissue retraction cooling device with serpentine internal flow channels, FIG. 4A (ii) shows a transparent front view of a rigid tissue retraction cooling device, FIG. 4A (iii) shows a transparent side view of a rigid tissue retraction cooling device, FIG. 4A (iv) shows a solid top view of a rigid tissue retraction cooling device with fluid tubing extending from the cooling device as the final assembly would include, FIG. 4A (v) shows a transparent front view of a rigid tissue retraction cooling device with a large distal reservoir, and FIG. 4A (vi) shows a transparent perspective view of a rigid tissue retraction cooling device with fluid tubing and internal lumen support inserts.
Figure 4B:
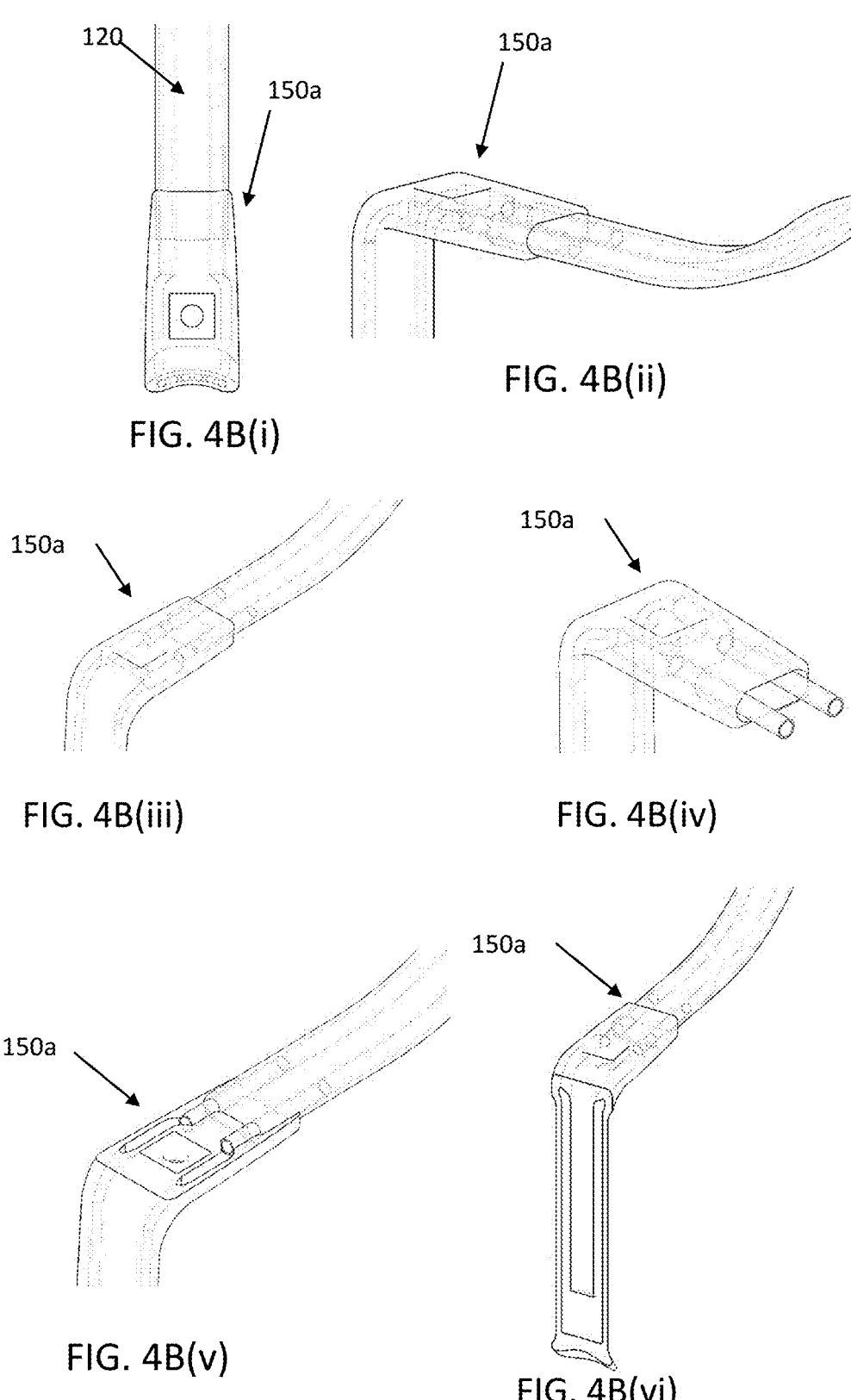
FIG. 4B (i) shows a transparent top view of a rigid tissue retraction cooling device with fluid tubing and lumen support inserts, FIG. 4B (ii) shows a transparent perspective of the same as 4B (i), FIG. 4B (iii) shows an alternate transparent perspective of the same as 4B (i), FIG. 4B (iv) shows a transparent perspective of the same as 4B (i) but without the fluid tubing to better illustrate the lumen support inserts, FIG. 4B (v) shows a transparent perspective section view of the rigid cooled retractor blade cooling device with the lumen inserts and fluid tubing shown solid and the area around them sectioned, and FIG. 4B (vi) shows a transparent perspective section view of the rigid cooled retractor blade cooling device with rigid cooling blade sectioned to illustrate internal flow reservoir.

FIGS. 4A (i)-4A (vi) and FIGS. 4B (i)-4B (ii) illustrate an exemplary patient cooling device 150a that is formed of rigid material with internal fluid conduits to allow fluid circulation from an attached cooling system 100/200/300 to cool the rigid material. It should be appreciated that the patient cooling device 150a shown in FIGS. 4A(i)-4A(vi) and 4B(i)-4B(vi) is for use with any of the cooling systems described previously (e.g., cooling system 100, 200, and/or 300). The forms and shapes of patient cooling device 150 can be interpreted to vary in any dimension of height width or length, and may have additional curvature or flat areas extended from any surface to maintain the same functional characteristics and provide additional shapes for clinical application to patient tissue.

FIG. 4A (i) shows a perspective transparent view of a rigid tissue retraction cooling device 150a with serpentine internal flow channels, FIG. 4A (ii) shows a transparent front view of a rigid tissue retraction cooling device 150a, FIG. 4A (iii) shows a transparent side view of a rigid tissue retraction cooling device 150a, FIG. 4A (iv) shows a solid top view of a rigid tissue retraction cooling device 150a with fluid tubing extending from the cooling device 150a as the final assembly would include, FIG. 4A (v) shows a transparent front view of a rigid tissue retraction cooling device 150a with a large distal reservoir, and FIG. 4A (vi) shows a transparent perspective view of a rigid tissue retraction cooling device 150a with fluid tubing and internal lumen support inserts. FIG. 4B (i) shows a transparent top view of a rigid tissue retraction cooling device 150a with fluid tubing 120 and lumen support inserts, FIG. 4B (ii) shows a transparent perspective of the same as 4B (i), FIG. 4B (iii) shows a alternate transparent perspective of the same as 4B (i), FIG. 4B (iv) shows a transparent perspective of the same as 4B (i) but without the fluid tubing 120 to better illustrate the lumen support inserts, FIG. 4B (v) shows a transparent perspective section view of the rigid cooled retractor blade cooling device 150a and with the lumen inserts and fluid tubing shown solid and the area around them sectioned, and FIG. 4B (vi) shows a transparent perspective section view of the rigid cooled retractor blade cooling device 150a with rigid cooling blade sectioned to illustrate internal flow reservoir.

Figure 5C:
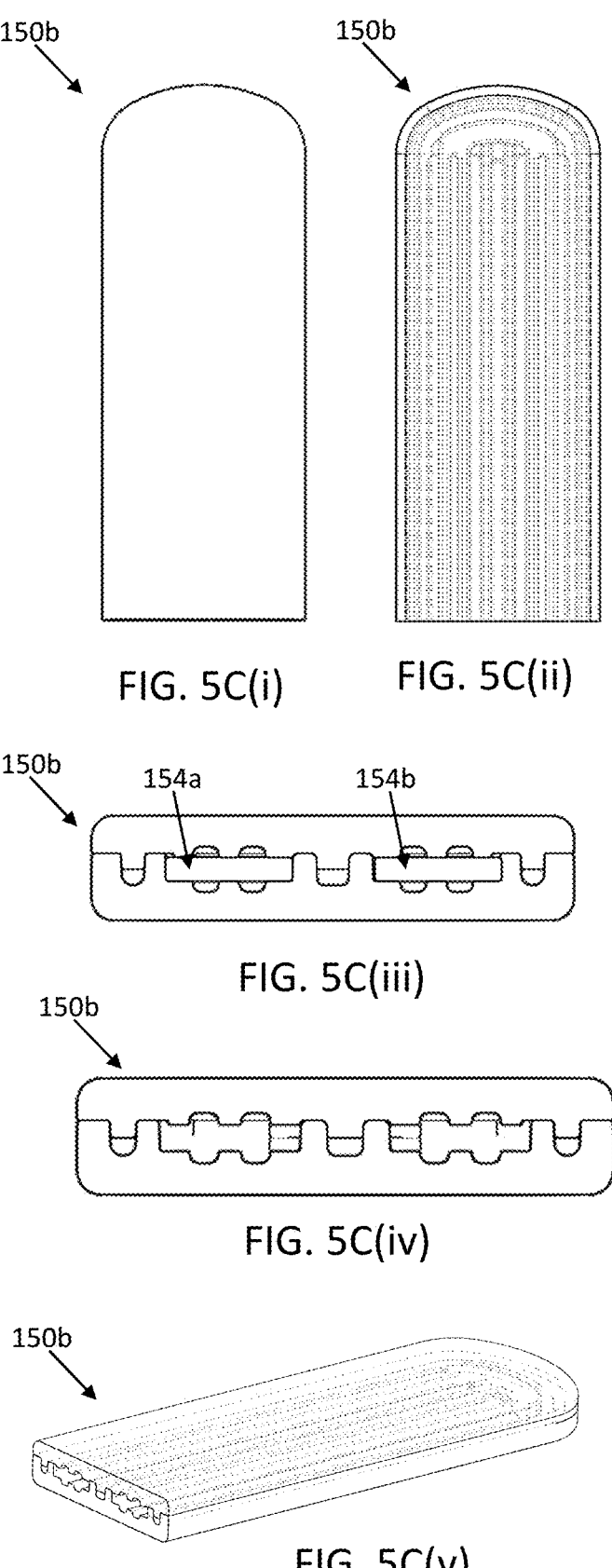
FIG. 5C (i) shows a solid top view of a mid-section cutaway view of the device, FIG. 5C (ii) shows a transparent top view of a mid-section cutaway exposing the fluid path structure and stiffener retaining features below, FIG. 5C (iii) shows a front view into a mid-section cutaway of the cooling device assembly with two malleable stiffeners shown and fluid conduits above and below the stiffeners, FIG. 5C (iv) shows a front view into a mid-section cutaway of the cooling device assembly without any malleable stiffeners, and FIG. 5C (v) shows a transparent perspective view of the same mid-section cutaway of the cooling device without any malleable stiffeners.

FIGS. 5A (i)-5A (iii), FIGS. 5B (i)-5B (iii) and FIGS. 5C (i)-5C (v) illustrate an exemplary patient cooling device 150b formed of two malleable material pieces with internal fluid conduits to allow fluid circulation from the cooling system to cool the malleable material. Optional malleable stiffening elements are shown in some illustrations, but may or may not be present. Similar to patient cooling device 150a, patient cooling device 150b may be used with any of the cooling systems described previously (e.g., cooling system 100, 200, and/or 300). The forms and shapes illustrated can be interpreted to vary in any dimension of height width or length, and have additional curvature or flat areas extended from any surface to maintain the same functional characteristics and provide additional shapes for clinical application to patient tissue.

FIG. 5A (i) shows a solid top view of a malleable tissue cooling device 150b with fluid tubing 120 and additional rigid mount 152 for attachment to a surgical mount system. FIG. 5A (ii) shows a side view of the patient tissue cooling device 150b shown in FIG. 5A (i), and FIG. 5A(iii) shows a perspective view of the patient tissue cooling device 150b. FIG. 5B (i) shows a top view of patient tissue cooling device 150*b* with two additional rigid stiffening elements 154*a*, 154*b* disposed inside of the fluid conduits and supported by unique structures above and below the malleable stiffeners 154*a*, 154*b*. FIG. 5B (ii) shows the same as (i) but without both stiffeners. FIG. 5B (iii) shows the same patient tissue cooling device 150*b* in perspective view with only one malleable stiffener 154*a*.

FIG. 5C (i) shows a solid top view of a mid-section cutaway of patient tissue cooling device 150*b*. FIG. 5C (ii) shows a transparent top view of a mid-section cutaway of patient tissue cooling device 150*b*, in which the fluid path structure is exposed and stiffener retaining features are positioned below. FIG. 5C (iii) shows a front view into a mid-section cutaway of the cooling device assembly 150*b* with two malleable stiffeners 154*a*, 154*b* and fluid conduits above and below the stiffeners.

FIG. 5C (iv) shows a front view into a mid-section cutaway of the cooling device assembly 150*b* without any malleable stiffeners and FIG. 5C (v) shows a transparent perspective view of the same mid-section cutaway of the cooling device 150*b* without any malleable stiffeners.

FIGS. 6A (i)-6A (ii) illustrate an exemplary patient cooling device 150*c* that is comprised of a malleable patient cooling device 156, or pad, adhered to the flat side of a rigid or malleable patient tissue retractor blade 158. The malleable pad 156 is cooled internally with closed-loop flow received from the cooling system 100/200/300, and transfers thermal energy from the retractor blade 158 material to the cooled liquid resulting in the retractor blade 158 material being cooled, in addition to patient tissue in contact with the cooled pad 156.

FIG. 6A (i) shows a solid front view of a malleable tissue cooling device 150*c* adhered to a rigid or malleable retractor blade 158 with fluid tubing 120 extending from the cooling device. FIG. 6A (ii) shows a solid side view of a malleable tissue cooling device 150*c* adhered to a rigid or malleable retractor blade 158 with fluid tubing 120 extending from the cooling device 150*c*.

In some embodiments, retractor blade 158 may be formed by three-dimensional (3-D) printing methods. Retractor blade 158 may be formed to include an internal fluid reservoir and supply/exhaust conduits to permit fluid to pass through. In some embodiments, the internal fluid reservoir of the retractor blade 158 may be greater than 50 rA. The internal fluid reservoir walls may be comprised of a tissue contacting wall and a tissue non-contacting wall. In these and other embodiments, the fluid conduits within the retractor blade 158 may continue within the blade from the internal fluid reservoir out of the proximal end of the blade. The proximal end of the blade may be bent between 70 and 110 degrees, in some embodiments, while in other embodiments, the proximal end of the blade may be bent to approximately 90 degrees. The supply conduit and exhaust conduit of the retractor blade 158 may be located around a mounting location hole and exit at the proximal end of the retractor blade 158. In some embodiments, the mounting location hole may be located on a proximal end bent approximately 90 degrees from the blade tissue contact surface.

FIGS. 7A (i)-7A (iv) illustrate an exemplary method of assembling a patient cooling device 150 and novel delivery sheath 160. It will be appreciated that any type of patient cooling device 150 discussed herein, for example, device 150*a*, 150*b*, or 150*c* may be used. The cooling device 150 is placed inside of a sheath 160 that has a closed end for insertion through an incision in patient tissue. This assembly becomes the delivered device to the patient and the sheath 160 is removed from within a primary open incision and the cooling device 150 is placed at the surgical site, where the primary incision is closed and the secondary incision continues to supply temperature controlled closed-loop fluid to the patient cooling device 150. FIG. 7A (i) shows a solid side view of a malleable tissue cooling device 150 with fluid tubing 120 extending from it being positioned to be inserted into the delivery sheath 160, Specifically, FIG. 7A (ii) shows a transparent side view of a malleable tissue cooling device 150 with fluid tubing 120 extending from it positioned inside of the delivery sheath 160. FIG. 7A (iii) shows a transparent side view of the sheath 160 only with additional texturing features and closed distal end and FIG. 7A (iv) shows a solid perspective view of the sheath 166 only with additional texturing features and closed distal end.

Figure 8A:
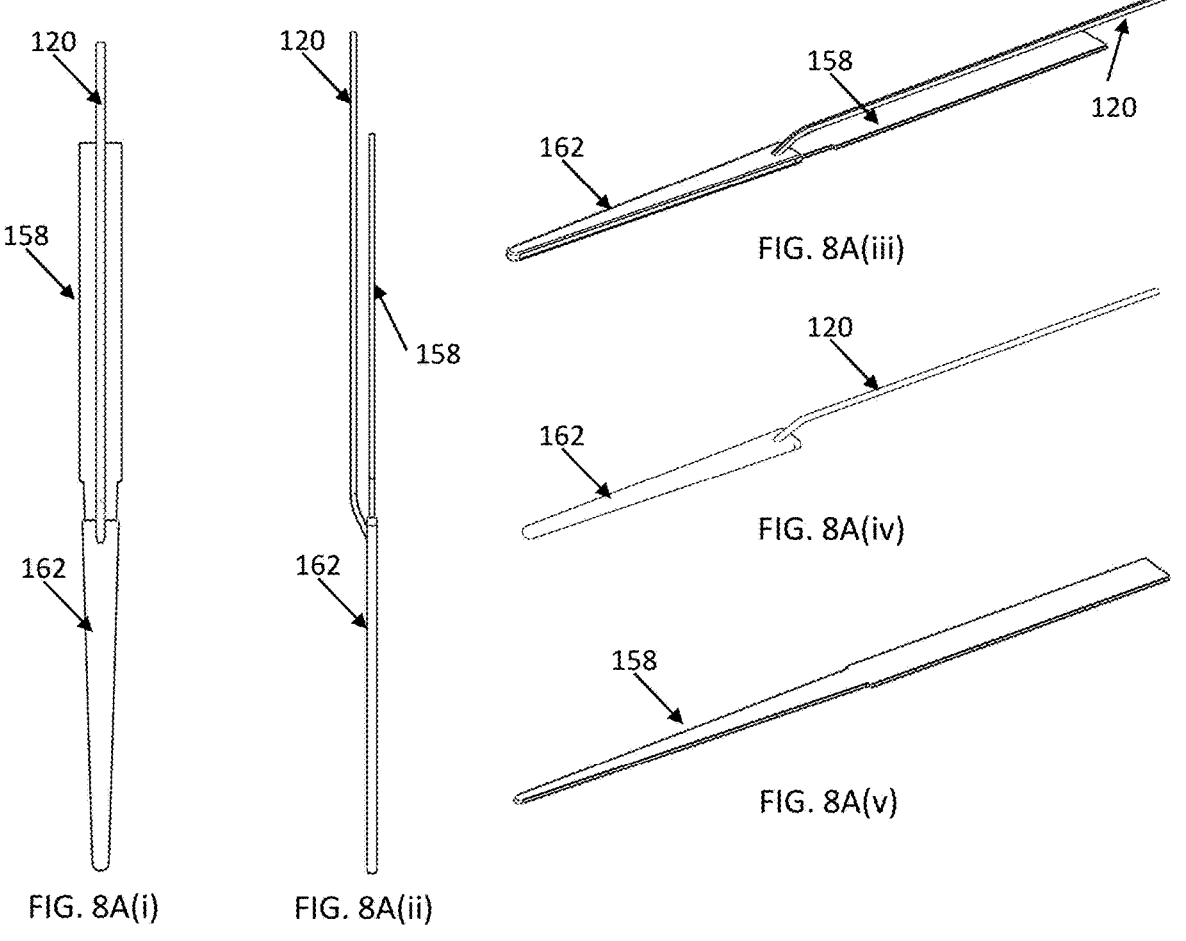
FIGS. 8A (i)-8A (v) illustrate an exemplary method of assembling a patient cooling device using a rigid or malleable retractor blade and novel cooling sheath, where a fully contained cooling sheath is placed over the retractor blade.

FIGS. 8A (i)-8A (v) illustrate an exemplary method of assembling a patient cooling device using a rigid or malleable retractor blade 158 and novel cooling sheath 162, where a fully contained cooling sheath 162 is placed over the retractor blade 158. The cooling sheath 162 has fluid tubing 120 extending to provide closed-loop flow of temperature-controlled fluid to the cooling sheath 162, which cools patient tissue that is in contact as well as the retractor blade 158. This same illustration can be used to describe an alternate configuration where an open cooling sheath 162 is placed over the retractor blade 158 and a seal is created on the proximal side around the retractor blade 158, using adhesive, an O-ring, or another stretch-fit material.

FIG. 8A (i) shows a solid front view of a cooling device assembly that includes a cooled malleable sheath 162 positioned over a rigid or malleable retractor blade 158 with fluid tubing 120 extending from the cooled sheath 162. FIG. 8A (ii) shows a solid side view of a cooling device assembly shown in FIG. 8A(i). FIG. 8A (iii) shows a solid perspective view of a cooling device assembly shown in FIGS. 8A(i) and 8A(ii). FIG. 8A (iv) shows a solid perspective view of only the cooled sheath 162 and FIG. 8A (v) shows a solid perspective view of only rigid or malleable retractor blade 158.

FIGS. 8B (i)-8B (ii) illustrate an exemplary method of assembling a patient cooling device using a rigid or malleable retractor blade 158 and novel cooling sheath 162, where an open cooling sheath 162 is placed over the retractor blade 158 and a seal is created on the proximal side around the retractor blade 158 using a rigid or malleable insert configured to receive the thin slot shape of a standard sheet metal retractor blade 158 and plug seal the open end of the open cooling sheath 162. The cooling sheath 162 has fluid tubing 120 extending to provide closed-loop flow of temperature-controlled fluid to the cooling sheath 162, which cools patient tissue that is in contact as well as the retractor blade 158. Specifically, FIG. 8B (i) shows a solid side view of a cooling device assembly comprised of cooled malleable sheath 162 and secondary blade receiving plug 164, over a rigid or malleable retractor blade 158 with fluid tubing 120 extending from the cooled sheath 162. FIG. 8A (ii) shows a perspective view of the assembly shown in FIG. 8B (i).

FIGS. 9A (i)-9A (vii) illustrates an exemplary method of assembling a patient cooling device using a rigid, flexible or malleable patient surgical scope 166 and novel cooling sheath 162, where a fully contained malleable cooling sheath 162 is placed over the scope 166. The cooling sheath 162 has fluid tubing 120 extending to provide closed-loop flow of temperature-controlled fluid to the cooling sheath, which cools patient tissue that is in contact as well as the scope 166.

FIG. 9A (i) shows a solid side view of a cooling device assembly comprised of cooled malleable sheath 162 with open end and over a rigid or malleable, flexible or rigid surgical scope 166, with fluid tubing 120 extending from the cooled sheath 162. FIG. 9A (ii) shows a transparent side view of the same assembly as FIG. 9A (i), FIG. 9A (iii) shows a transparent side view of the cooling pad sheath 162 with a conical distal end for insertion through tissue, FIG. 9A (iv) shows a solid side view of the same assembly with a split open flat design that is wrapped around the scope 166 and secured with a self-adhering strap. FIG. 9A (v) shows a solid perspective view of the same assembly as in FIG. 9A (iv). FIG. 9A (vi) shows a solid side view of the same assembly with temperature sensor 111 disposed inside the cooling device reservoir. FIG. 9A (vii) shows a front solid view of an unfolded cooling sheath 162 with serpentine fluid path.

FIGS. 10A (i)-10A (iii) illustrate an exemplary patient cooling device assembly 150*d* with over-molded cap assembly, optional malleable stiffening elements, fluid tubing 120 and coupler 168 to a cooling system 100/200/300. FIG. 10A (i) shows a perspective solid view of the entire cooling device assembly 150*d* including between 1 and 10 feet of fluid tubing 120, with the patient contact side on the right side and coupler 168 to cooling system 100/200/300 on the left side, where the coupler assembly 168 includes a mechanism to auto-lock the coupler once connected to the cooling system 100/200/300 as well as features to allow blind and reversible connection. FIG. 10A (ii) shows a solid top-plane cut-away top view of the patient contact portion of the cooling device assembly 150*d* illustrating the internal layout and assembly including a formed tubing in a U turn shaped inserted into both outer lumens which carry return and supply cooled fluid from the cooling system 100/200/300, where the U-shape has a relatively high melting temperature that allows over-molding of the cap as shown, and two optional malleable stiffeners occupy one or more of the center lumens, and FIG. 10A (iii) shows a solid transparent top view of the patient contact portion of the cooling device assembly 150*d* described in FIG. 10A (ii).

FIGS. 10B (i)-10B (iii) illustrate an exemplary patient cooling device assembly 150*d* with alternate cap assembly, lumen support tubing which may have partial or complete cutaways on the interior surfaces facing the reservoir, optional malleable stiffening elements, fluid tubing, and coupler 168 to cooling system 100/200/300. Specifically, FIG. 10B (i) shows a perspective solid view of the entire cooling device assembly 150*d* including between 1 and 10 feet of fluid tubing 120, with the patient contact side on the right side and coupler 168 to cooling system 100/200/300 on the left side, where the coupler assembly 168 includes a mechanism to auto-lock the coupler 168 once connected to the cooling system 100/200/300 as well as features to allow blind and reversible connection. FIG. 10B (ii) shows a solid perspective view of the patient contact portion of the cooling device assembly 150*d* illustrating where the cap is inserted into and permanently adhered or welded to the end of the extrusion to create closed-loop fluid flow between the cooling device 150*d* and cooling system 100/200/300. FIG. 10B (iii) shows a transparent perspective view where the separate rigid or malleable cap is a second piece that is attached and welded or sealed around the perimeter of the joint between the cap and the tubing and where there are two formed tubing pieces with higher melting temperature where the tubing pieces are between 220 and 330 degrees of tubing and between 120 and 30 degrees of at least partially open wall that faces the interior reservoir on each side of the fluid lumen. FIG. 10B (iv) shows a perspective solid view of both formed tubing pieces in free air as they would be positioned in the assembly 150*d*. FIG. 10B (v) shows a perspective solid top-plane cut-away view of the fluid tubing and secondary cap. FIG. 10B (vi) shows a perspective solid top-plane cut-away view of the fluid tubing and secondary cap where the optional stiffeners and outer formed tubing are shown in full form. FIG. 10B (vii) shows a perspective solid top-plane cut-away view of the fluid tubing and secondary cap where the optional stiffeners and alternate outer formed tubing are shown in full form.

FIGS. 11A (i)-(iv) illustrate an exemplary patient cooling device assembly 150*e* that is comprised of a rigid retractor blade shim insert with internal reservoir and fluid tubing 120 extending from shim. A non-cooled traditional retractor blade 158 with corresponding slots is used to retract tissue during surgery, and shims of different sizes shapes and functions are placed down the retractor blade slot and locked in place or otherwise loose. The cooled shim 170 cools tissue that it contacts as well as the retractor blade 158 which in turn cools additional patient tissue. Specifically, FIG. 11A (i) shows a perspective solid view of a cooled shim 170 with a pointed end that has been inserted down a traditional slotted tissue retractor blade 158 and fluid tubing 120 extends from the shim 170. FIG. 11A (ii) shows a perspective transparent view of the same as FIG. 11A (i), FIG. 11A (iii) shows a front transparent view of the same as FIG. 11A (i), and FIG. 11A (iv) shows a side transparent view of the same as FIG. 11A (i).

Methods of Use

The disclosed cooling systems and patient tissue cooling devices can be used in a multitude of ways for a variety of different surgical purposes. For example, in some embodiments, the disclosed systems, devices, and/or methods may be used in connection with surgical procedures involving one or more of the following: the spine, the brain, procedures in which tissue is adversely affected from surgical retraction pressure, such as during tissue retraction procedures, including retraction of nerves, blood vessels, organs, muscles, and/or fascia. In some embodiments, the disclosed systems, devices, and/or methods may be used in surgical procedures to cool any internal organs and/or other patient tissue that has seen trauma or is at risk of damage or traumatization. In select embodiments, the disclosed devices, methods, and systems may be used for brain tissue contact, such as when lobes of the brain are contacted (e.g., flat retractor blade inserted into a cranial incision or craniotomy; retract complete lobes of the brain or retract neural tissue along a surgical incision into the neural tissue). In some embodiments, the use of a any of the disclosed cooling devices may be prophylactic (for example, cooling tissue prior to retraction or cooling for a short duration of time to allow sufficient thermal effects to the tissue). In some embodiments, a malleable cooling device can be applied and contoured to cool any tissue. In some embodiments, thermal therapy is continued post-operatively. Select example methods are described in detail below to illustrate possible uses of the presently disclosed subject matter.

In a first example embodiment of applying thermal therapy to a target area of a patient tissue during surgery, the following steps are performed: connecting a power source to a control unit, connecting a signal cable to a refrigeration unit, connecting a tubing kit and a thermal therapy device to the refrigeration unit to create a closed-loop circuit, filling the tubing kit and the thermal therapy device with a sterile fluid, placing the thermal therapy device in contact with the target area of patient tissue, and activating the refrigeration unit to circulate the sterile fluid through the thermal therapy device and the tubing kit. In some embodiments, the thermal therapy device is placed in contact with the target area of patient tissue before the refrigeration unit is activated. In some embodiments, the refrigeration unit is activated before the thermal therapy device is placed in contact with the target area of patient tissue. In some embodiments, the sterile liquid is pure water or saline. The thermal therapy device may be placed in contact with the target area of patient tissue before the refrigeration unit is activated. The thermal therapy device may be placed in contact with the target area of patient tissue after the refrigeration unit is activated. The closed-loop circuit may include: a length of flexible tubing, internal connectors attaching the length of flexible tubing to the refrigeration unit, a tubing kit connector attaching the length of flexible tubing to the thermal device, one or more tubing fill ports in fluid communication with the length of flexible tubing, one or more a multi-lumen extrusions (i.e., an extruded tubing defining a plurality of lumens therein), thermal device interior walls, temperature sensors or sensor fittings, a thermal exchange plate, a thermal exchange plate cap, and a pump positioned to circulate fluid throughout the closed-loop circuit. The thermal exchange plate may be positioned in contact with the thermoelectric element. The thermal exchange plate cap may be positioned in contact with the thermal exchange plate. The thermal device interior walls may have an outer surface defining exterior walls of the device and the exterior walls of the device may be configured to be placed into direct contact with patient tissue. The length of flexible tubing can include at least two separate flow paths, each in fluid communication with the thermal device. The length of flexible tubing may include two separate flow paths, each formed by a lumen, and a separate lumen formed to accommodate a malleable wire. A second length of flexible tubing may be attached to the thermal device and to the refrigeration unit. The closed-loop circuit may include two tubing fill ports attached to the length of flexible tubing. An outer surface of the thermal device interior walls may contact the target area of patient tissue. The closed-loop circuit may include more than 90% liquid and less than 10% air after the tubing kit and the thermal therapy device are connected and filled.

In a second example embodiment, a method of applying thermal therapy to a target area of patient tissue during surgery includes the following: connecting a power plug of a refrigeration unit to a power source, wherein the refrigeration unit is connected to a tubing kit and a thermal therapy device to create a closed-loop circuit, filling the refrigeration unit, tubing kit, and thermal therapy device with a sterile fluid, placing the thermal therapy device in contact with the target area of patient tissue, and activating the refrigeration unit to circulate the sterile fluid. The refrigeration unit, tubing kit, and thermal therapy device may be filled with the sterile fluid by pumping liquid into the system and expelling air and liquid into a reservoir for disposal. The refrigeration unit, tubing kit, and thermal therapy device may be filled with the sterile fluid by expelling air from a first section of the tubing kit and drawing in the sterile fluid through a second section of the tubing kit using negative pressure generated by the extraction of air.

In a third example embodiment, a method of filling a cooling system and patient cooling device comprising a length of flexible tubing, a first port, and a second port, includes the following: removing a first cap from the first port, removing a second cap from the second port, connecting an empty, collapsed disposal bag to the first port, connecting a fill tube to the second port, placing the fill tube in contact with a sterile fluid, expanding the syringe to pull sterile fluid into the flexible tubing, removing the syringe and filling the flexible tubing with the sterile fluid, placing the first cap onto the first port, placing the second cap onto the second port to form a closed-circuit length of flexible tubing filled with the sterile fluid, removing a sterile pad, tubing, cassette, and saline supply tubing from packaging, connecting a proximal end of the pad and tubing connector into a cassette top, connecting a luer-end of the saline supply tubing to fill port on pad and tubing, connecting a spike-end of saline supply tubing into a saline bag, connecting a luer-tipped syringe to draw port on the pad and tubing, and operating a syringe to create a vacuum within the closed system to fill with saline.

The cooling device and tubing may be permanently attached to a length of fluid tubing. The cooling device may be sterile. In other embodiments, the cassette functions as the refrigeration unit. In some embodiments, the saline supply tubing includes a luer fitting, single-lumen tubing, and a saline spike.

The closed-circuit system may have a volume of between 20 cc and 200 cc. The method may also include disconnecting the syringe from the system and disposing of the syringe. The method may also include rotating knobs, capping ports and disposing of saline supply tubing and disposal overflow fill bag.

In another example embodiment, a method of filling a cooling system and patient cooling device comprising a length of flexible tubing, a first port, and a second port, a patient cooling device and cooling refrigeration unit includes the following: connecting a patient device coupler to a refrigeration unit fluid tubing coupler, powering on the system, connecting a port with tubing and spike to a source of liquid, initiating fluid fill system state where electrical software control of the pump fills the system and cooling device by pumping fluid and air through the system. This is accomplished by expelling air out of the I' section of tubing and creating negative pressure in the 2nd section of tubing, where the air and liquid is expelled out of a $2^{nd}$ port into a vessel that may be expandable which creates a different pressure inside of the disposal vessel than atmospheric pressure. The disposal vessel or bag may have one or more check valves to prevent backflow of air and liquid. The software state may manually or automatically terminate, and the disposal vessel and tubing with spike are removed from the system and two caps are tightly secured to the two ports.

In a fourth example embodiment, a method of forming a blade is described. The blade may include two opposing halves that are bonded along a circumferential channel and a center channel where an extrusion with 2 or more fluid lumens is bonded. An extrusion with 2 or more lumens is bonded to the blade by: inserting a single lumen tubing into each fluid lumen of the extrusion and placing an extrusion assembly into one half of malleable blade, wherein the extrusion is laid into a track and the track accommodates half of the single lumen tubing and the other half protrudes above the surface of the malleable blade half. Adhesive is applied over outer surface of single lumen tubing and the top half of malleable blade is placed onto the extrusion assembly with adhesive and the bottom half. Additional adhesive may be placed into additional channels in the bottom half to fully attach the top half of the malleable blade such that the channels are circumferential and midline.

In a fifth example embodiment, a patient tissue cooling device as previously described herein is placed in the cervical spine to retract esophageal tissue. Cooling may be applied prior to retraction to provide reduction of dysphagia and decreased recovery time. In other embodiments, the patient tissue cooling devices described herein may be placed in the lateral spine to retract nerve and muscle. In some such embodiments, cooling may be applied prior to retraction to provide reduction of neuropathy and decreased recovery times. In yet further embodiments, the disclosed patient tissue cooling devices may be used for posterior access procedures or any surgical access whether open, semi-open, minimally invasive or percutaneous. The effect of local cooling devices may be to reduce tissue trauma, reduce infection rate and decrease recovery time.

In a sixth example embodiment, a malleable blade for general surgical or cranial applications is disclosed. The malleable blade includes an internal fluid reservoir, a supply conduit, and an exit conduit, each in fluid communication with the fluid reservoir. The blade is bendable and malleable in that a human hand can adjust the shape of the device. The blade may be configured to bend only in one plane (uniplanar). In some such embodiments, the bending direction is perpendicular to the direction of retraction. The blade may be formed of a biocompatible plastic extrusion with supply and exhaust conduits. The reservoir of the blade may include the supply conduit and the exhaust conduit. The blade may include one or more bendable metal wires placed within. The bendable metal wires may be copper, in some embodiments, and may be flat. The distal end of the device is comprised of a conduit connecting cap that is attached to the blade extrusion. The conduit cap is formed of a half toroid metal tubing contained partially within both supply and exhaust conduits and encapsulated within the conduit cap. A mounting attachment may be affixed to the blade. If present, the attachment may have a C-shape that is slid over and contains the two assembled halves of the blade. Additional embodiments may make use of one or more individual lumen support tubings that are straight with interior portions exposed or removed to allow flow to an interior portion of reservoir, with a secondary cap added to create a closed-loop flow within the device.

EXAMPLES

The following are various example embodiments that are provided for illustration purposes. The full scope of the subject disclosure is not intended to be limited by the particular example embodiments described herein.

Example 1: Self-Contained Patient Tissue Cooling System

In this example, a self-contained patient tissue cooling system includes a housing, a thermoelectric element (TEC) in thermal communication with a heat exchanger, a fluid pump in fluid communication with a fluid inlet and a fluid outlet, a fluid cooling element in thermal contact with the thermoelectric element, a fan, a power connector, a temperature sensor, a power controller to adjust cooling power to the thermoelectric element, a power switch, a power filter, an AC to DC power supply, a fluid connector to the patient cooling device, and a user interface.

Example 2: Patient Tissue Cooling System

In this example, a patient tissue cooling system includes a refrigeration unit housing and a control unit housing. The refrigeration unit housing includes a thermoelectric element in thermal communication with a heat exchanger, a fluid pump in fluid communication with a fluid inlet and a fluid outlet, a fluid cooling element in thermal contact with the thermoelectric element, a fan, a fluid connector to the patient cooling device, a temperature sensor, a power and signal connector, and a user interface. The control unit housing includes a power connector, a power and signal connector, a power controller to adjust cooling power to the thermoelectric element, and a power switch.

In some embodiments of example 1 and/or example 2, the fluid cooling element may be a plate. The fluid may be a liquid. The thermoelectric element may be encapsulated. The fluid cooling element and thermoelectric element may be in contact with insulation. In some such embodiments, the insulation may be closed cell foam. In these and other embodiments, 5 sides of the cooling element and the thermoelectric element assembly may be surrounded by foam and the $6^{th}$ side may not be in contact with the foam.

The components may be internally supported and in contact with a sub-frame, in some embodiments. In some such embodiments, the frame may be comprised of sheet metal. The heatsink may be thermally decoupled from the enclosure housing via the sub-frame. In these and other embodiments, insulating material may be disposed between the heatsink and the frame.

The components within the refrigeration unit housing that are in fluid communication may include: a pump, temperature sensor(s), a fluid cooling element, a fluid inlet, and/or a fluid exhaust. The fluid path between these components may create a closed-loop flow when connected to a cooling device.

The temperature sensors may include a thermistor probe disposed inside of a metal sheath. The metal sheath and probe assembly may reside inside of a plastic fluid fitting. The fitting may have a T shape. The probe assembly may be inserted into one first opening in the fitting such that fluid passes over the sensor assembly as fluid flows into the second opening and out of the third opening. In some such embodiments, no fluid may flow out of the first opening. In these and other embodiments, the fitting and probe assembly may be fluid sealed using one or more layers of wrapping. The wrapping may be glued or bonded using heat. The temperature sensor and fitting assemblies may be positioned in the refrigeration unit housing where the sensor probe is angled above the horizontal plane (0°) at least 1 degree with the probe tip pointing upward.

In some embodiments, a Printed Circuit Board may be positioned inside of the refrigeration unit housing. A strain relief may retain the power signal cable inside of the refrigeration unit housing. In some such embodiments, the strain relief may allow the cable to exit the bottom of the housing at an angle greater than 15°.

The user interface may include a temperature display, in some embodiments. The temperature may be shown as a two-digit numeric display. The temperature shown may be the calculated temperature of the patient cooling device. The temperature shown may be the calculated temperature of the fluid inside of the patient cooling device.

The patient cooling device may be a retractor blade with internal fluid paths, a bone screw with internal fluid paths, a tissue cooling pad with internal fluid paths, or any other implant or instrument made compatible with the cooling system.

In some embodiments, the power may be controlled via a processor. The processor may measure temperatures inside of the refrigeration unit. In some embodiments, multiple temperatures may be measured. The processor may calculate the temperature of the fluid in the device at the patient. The processor may also calculate power delivery based on heat exchanger temperature and/or ambient temperature.

In some embodiments, the power may be controlled via a temperature feedback loop. The heat exchanger may be a passive air heat exchanger or an active air heat exchanger. The heat exchanger may be an active liquid heat exchanger or a passive liquid heat exchanger. The heat exchanger may also include one or more temperature sensors positioned to measure a temperature at the liquid inlet, at the liquid outlet, at a position between the liquid inlet and the liquid outlet and/or temperature of the heat exchanger.

The user display may be configured to display: a measured temperature of fluid within the refrigeration unit, a temperature setting control, and/or a status indicator for the refrigeration unit. In some embodiments, the temperature setting control may adjust the thermoelectric element (for example, by changing the power supplied to the thermoelectric element). In other embodiments, the temperature setting control may adjust the flow rate of the liquid.

The cooling device may include a fan positioned to pull air into the refrigeration unit. If present, the fan may be an axial fan. In some embodiments, the fan may be centrifugal. The fan may be positioned to expel air from a bottom region of the refrigeration unit. In some embodiments, air may be expelled from the back and/or sides of the enclosure. Air may be pulled through an EMI filter prior to entering the enclosure, in some embodiments. The EMI filter may be a passive grate. The EMI filter may be comprised of a plurality of holes or slots formed in the material and/or in a separate piece. In select embodiments, the fan may include an EMI filter formed in an add-on piece and the air inlet material may include a patterned EMI integrally formed therein. The heat exchanger may be a passive air heat exchanger and the refrigeration unit may also include a liquid heat exchanger. Air exiting the enclosure may pass over both the liquid heat exchanger and the passive air heat exchanger.

In some embodiments, a secondary fan is placed in close proximity to the heat exchanger internal to the refrigeration unit housing.

The user display may be configured to provide feedback on a status of the patient tissue cooling system. The user display may include one or more lights, which indicate a cooling state of the patient tissue cooling system. The cooling state may be a set temperature and/or a power level.

The user display may include a numeric display, which provides feedback on the liquid temperature. The user display may include one or more user input buttons, which adjust the controller, and in turn the power delivered to the thermoelectric element in contact with the liquid cooling plate, to a desired liquid and/or device temperature. Any number of user interface elements may be used to select and/or adjust the temperature (e.g., buttons, dials, sliders, or other manually selectable features either in a physical medium or in a graphical user interface).

In some cases, the power filter may be a dual stage power filter. Leakage current after the power filter may be less than 5 uA. The power filter may have a Capacitance (Cx) of between 100 and 300 nF. The power filter may have a Resistance of between 500 and 1500 kOhm. The power filter may reside in a separate filter box outside the housing and a single DC power line may connect the filter box to the housing. In some such embodiments, the filter box may also contain the controller.

The cooling device may include a tubing kit having an attached patient contacting thermal device, wherein the tubing kit and the attached thermal device are both fixedly attachable to the refrigeration unit. The refrigeration unit and cooling device may be single-use (i.e., disposable), in some embodiments. The refrigeration unit may be sterile. The cooling device may be sterile.

Example 3: Methods of Applying Thermal Therapy to a Target Area

In this example, methods of applying thermal therapy to a target area of patient tissue during surgery are described. The methods include connecting a power source to a control unit, connecting a power/signal cable from control unit to refrigeration unit [having the features recited above], connecting a tubing kit and a thermal therapy device to refrigeration unit to create a closed-loop circuit, filling the tubing kit and the thermal therapy device and refrigeration unit with a sterile fluid, placing the thermal therapy device in contact with the target area of patient tissue, and activating the refrigeration unit to circulate the sterile fluid through the refrigeration unit, thermal therapy device and the tubing kit.

In some embodiments, the thermal therapy device is placed in contact with the target area of patient tissue before the refrigeration unit is activated. In some embodiments, the refrigeration unit is activated before the thermal therapy device is placed in contact with the target area of patient tissue The closed-loop circuit may include a length of flexible tubing, one or more connectors attaching the length of flexible tubing to the refrigeration unit, a tubing kit connector attaching the length of flexible tubing to the thermal device, one or more tubing fill ports attached to the length of flexible tubing, a multi-lumen extrusion (i.e., an extruded tubing defining a plurality of lumens therein), thermal device interior walls, temperature sensor fittings, a thermal exchange plate, a thermal exchange plate cap, and a pump positioned to circulate fluid throughout the closed-loop circuit.

The thermal exchange plate may be positioned in contact with the thermoelectric element. The thermal exchange plate cap may be positioned in contact with the thermal exchange plate.

The thermal device interior walls may have an outer surface defining exterior walls of the device. The exterior walls of the device may be configured to be placed into direct contact with patient tissue. An outer surface of the thermal device interior walls may contact the target area of patient tissue.

The length of flexible tubing may include at least two separate flow paths, each in fluid communication with the thermal device. The length of flexible tubing may include two separate flow paths, each formed by a lumen, and one or more separate lumens formed to accommodate a malleable wire. The length of flexible tubing may also include a second length of flexible tubing attached to the thermal device and to the refrigeration unit. The closed-loop circuit may include two tubing fill ports attached to the length of flexible tubing. The sensor fittings may be positioned in contact with the sterile fluid, may be part of the closed-loop fluid circuit, or may be positioned before and after the cooling plate.

The power source may originate from a 3-prong grounded AC plug. The closed-loop circuit may include air and not liquid after the tubing kit and the thermal therapy device are connected to the refrigeration unit. The sterile liquid may be saline or distilled water. The refrigeration unit may be single-use (i.e., disposable).

The thermal therapy device may be a retractor blade or a retractor blade shim (e.g., an extension shim or a fixation shim), a cooling pad, spinal implant, and/or bone screw.

The methods may also include adjusting a temperature of the sterile fluid in the thermal therapy device. The target area may be one or more nerves or may include the spinal cord and/or brain. The methods may be used in connection with a surgical procedure on the spine, the brain, and/or a procedure in which tissue is adversely affected from surgical retraction pressure (e.g., during tissue retraction of nerves, blood vessels, organs, muscles, and/or fascia).

Example 4: Methods of Applying Thermal Therapy
to a Target Area

In this example, methods of applying thermal therapy to a target area of patient tissue during surgery are described. The methods include connecting a power plug of a control unit (description per above) to a power source, connecting a power signal cable from control unit to refrigeration unit, wherein the refrigeration unit is connected to a tubing kit and a thermal therapy device to create a closed-loop circuit, filling the refrigeration unit, tubing kit, and thermal therapy device with a sterile fluid, placing the thermal therapy device in contact with the target area of patient tissue, and activating the refrigeration unit to circulate the sterile fluid. The refrigeration unit, tubing kit, and thermal therapy device may be filled with the sterile fluid by extracting air from a first section of the tubing kit and drawn in the sterile fluid through a second section of the tubing kit using negative pressure generated by the extraction of air. Also, the closed-loop circuit may be filled using a powered software mode in the system that activates the pump inside the refrigeration unit.

Example 5: Patient Tissue Cooling System
(Multi-Unit Console)

In this example, a multi-unit patient tissue cooling console is described. The console includes a plurality of powered cassette slots and a plurality of cassettes, each shaped to fit inside a powered cassette slot, wherein each cassette includes a complete closed-loop circuit comprising [elements as described in a closed-loop configuration] and a cooling device [having features described herein with respect to thermal therapy devices] connected to the control console.

The powered cassette slots may be vertically oriented. The powered cassette slots may each include a multi-connection electrical interface and at least one open hole. At least one open hole may be covered with a metal mesh. Each cassette may be independently controlled by a controller. Each cassette may have a temperature that may be controlled independently from the other cassettes. The closed-loop circulation of each cassette may be independent from the other cassettes. In some embodiments, upon providing power to the control console the plurality of cassettes, each individually may possess an initial power state in which the thermoelectric element, pump, and fan are all powered off. In these and other embodiments, after ceasing operation, the plurality of cassettes may each individually possess a completion power state that includes maintaining the fan power at nominal voltage and turning off power to the thermoelectric element and pump. The console includes a control unit, power filter, AC/DC power converter and connectors to interface with the cassettes.

Example 6: Methods of Filling a Patient Cooling
Device/System

In this example, methods of filling a patient cooling device/system are described. Some example methods include filling a tubing device having a length of flexible tubing, a first port, and a second port. In particular, the methods include removing a first cap from the first port, removing a second cap from the second port, connecting an empty, collapsed syringe to the first port, connecting a fill tube to the second port, placing the fill tube in contact with a sterile fluid, expanding the syringe to pull sterile fluid into the flexible tubing (wherein the syringe creates pressure differential within circuit to fill with the sterile fluid), removing the syringe and filling the flexible tubing with the sterile fluid, placing the first cap onto the first port, placing the second cap onto the second port to form a closed-circuit length of flexible tubing filled with the sterile fluid, removing a sterile Pad+Tubing, Cassette, and Saline Supply Tubing from packaging, connecting a proximal end of the Pad+Tubing Connector into a Cassette top, connecting a luer-end of the saline supply tubing to fill port on Pad+Tubing, connecting a spike-end of saline supply tubing into a saline bag, connecting a luer-tipped syringe to draw port on Pad+Tubing, and operating a syringe to create a vacuum within the closed system to fill with saline.

In some embodiments, the sterile pad and tubing refers to the thermal therapy device previously described herein that may be permanently attached to a length of fluid tubing. In these and other embodiments, the cassette functions as the refrigeration unit and the saline supply tubing may include a luer fitting, single-lumen tubing, and a saline spike. To fill the system, the cassette does not need to be powered on.

In some embodiments, the closed-circuit system may have a volume of between 20 cc and 200 cc that is drawn into the syringe to purge air from the system. The methods may also include disconnecting the syringe from the system and disposing of the syringe. In select embodiments, the methods may also include capping the tubing draw port and disposing of the saline supply tubing.

Example 7: Retractor Blade (3-D Printed)

In this example, a 3-D printed retractor blade is described. The tissue retraction blade may include an internal fluid reservoir and supply/exhaust conduits for liquid fluid. The surface roughness of the internal reservoir may be greater than 50 rA. The internal fluid reservoir walls may include a tissue contacting wall and a tissue non-contacting wall. The fluid conduits within the retractor blade may continue within the blade from the reservoir out of the proximal end of the blade.

The proximal end of the blade may be bent between 70 and 110 degrees. In some embodiments, the proximal end of the blade may be bent to approximately 90 degrees. In some embodiments, the distal end of the blade may be angled at up to 70 degrees. The supply/exhaust conduits may be located around a mounting location hole and exit the proximal end. The mounting location hole may be located on a proximal end bent approximately 90 degrees from the blade tissue contact surface.

The example retractor blade can be used in various surgical procedures. For example, the retractor blade may be placed in the cervical spine to retract esophageal tissue. In some such embodiments, cooling may be applied prior to retraction. In some such embodiments, cooling may reduce dysphagia and decrease recovery times.

In some embodiments, the retractor blade may be placed in the posterior spine or lateral spine to retract nerve and muscle. In some such embodiments, cooling may be applied prior to retraction. In some such embodiments, cooling may reduce neuropathy, infection rate, and/or decrease recovery times.

Example 8: Malleable Blade (Cranial)

In this example, a malleable tissue retraction blade is described. The retraction blade may be used for cranial or other surgical purposes. The tissue retraction blade includes an internal fluid reservoir, a supply conduit, and an exit conduit, each in fluid communication with the fluid reservoir.

The blade may be bendable and malleable in that a human hand can adjust the shape of the device. The bending may be in one plane (uniplanar). In these and other embodiments, the bending direction may be perpendicular to the direction of retraction.

The blade may include a biocompatible plastic extrusion with supply and exhaust conduits. The reservoir may include the supply conduit and the exhaust conduit. In some embodiments, one or more bendable metal wires may be placed within the extrusion. In some such embodiments, the metal may be copper and/or the metal wire(s) may be flat. The distal end of the device may include a conduit connecting cap attached to the blade extrusion. In some such embodiments, the conduit cap may include a half toroid metal tubing. In these and other embodiments, the tubing may be contained partially within both supply and exhaust conduits and encapsulated within the conduit cap.

The blade may include two opposing halves, in some embodiments. The halves can include a circumferential channel and a center channel. In some embodiments, the channels may interlock. The channels may create a loop circuit, in some embodiments. There may be a malleable metal within the fluid loop channels. In some such embodiments, the malleable metal may be copper and/or may be flat.

In some embodiments, a mounting attachment may be affixed to the blade. The attachment may have a C shape that is slid over and contains the two assembled halves of the blade.

The disclosed blades may be used in connection with any suitable surgical technique. For example, the blades may be used for brain tissue contact. In some such embodiments, the devices may be used in connection with lobes of the brain (e.g., flat retractor blade inserted into a cranial incision or craniotomy; retract complete lobes of the brain or retract neural tissue along a surgical incision into the neural tissue). The devices may be used for prophylactic purposes (e.g., cooling tissue prior to retraction; cooling for a short duration (3-5 minutes) to allow sufficient thermal effect to the tissue).

The blades can be manufactured by any desired technique. In some cases, the blade may be comprised of two opposing halves and the halves may be bonded along a circumferential channel and a center channel. In some embodiments, an extrusion with 2 or more fluid lumens may be bonded to the blade. In some embodiments, the blades can be formed by inserting a single lumen tubing into each fluid lumen of the extrusion and placing an extrusion assembly into one half of malleable blade. The extrusion may be laid into a track and the track may accommodate half of the single lumen tubing. In these and other embodiments, the other half may protrude above the surface of the malleable blade half. Adhesive may be applied over an outer surface of the single lumen tubing and the top half of the malleable blade may be placed on an extrusion assembly with adhesive and the bottom half. Additional adhesive may be placed into additional channels in the bottom half to fully attach the top half of the malleable blade. The channels may be circumferential and midline in some embodiments.

Example 9: Pad Attached to Blade

In this example, a pad attached to a blade (e.g., a retractor blade) is described. The device may be constructed by attaching a tubing pad to a (malleable or other) blade, rendering a cooled combination device. In some embodiments, the adhesion may be permanent. The retractor blade proximal end may consist of a cylindrical post extending from the blade surface. In some such embodiments, the blade may be malleable.

Example 10: Cooling Device Sheath on Pad

In this example, a cooling pad (as described herein) is contained within a hollow plastic sheath. The sheath may be comprised of an open tube with one end closed. The closed end may be pointed or bulleted. In select embodiments, the point may be larger than a 0.25 mm radius. The top and bottom surface of the plastic sheath may be substantially flat and the side may be substantially round. The top and bottom surfaces may have indentations that provide an interference fit between the sheath and the contained pad.

Example 11: Cooling Device Delivery Methods (Sheath)

In this example, a method of use for a cooling delivery device is described. The method includes creating access incision in a patient, placing a thermal device that has a sheath cover disposed thereover, inserting the thermal device with sheath through the patient access incision, removing the sheath from the thermal device from inside the incision, positioning the thermal device in contact with patient tissue, and providing thermal therapy to the patient.

In some embodiments, the thermal device may be an implant. In some embodiments, the thermal device may be a catheter. The access incision may be percutaneous/minimally invasive.

The sheath may be made of polymer. The sheath containing the cooling device may be inserted through a secondary incision to deliver the cooling device to the application site. In some such embodiments, the secondary incision may be the midline (sagittal plane) incision following the patient's spinal column. The sheath may be removed from the thermal device through the primary surgical incision. In some such embodiments, the primary incision can be closed to leave the cooling device at the application site, and the cooling device may be removed without reopening the surgical incision.

Example 12: Pad Design Elements

Various design elements of exemplary pads are described herein. In some embodiments, the pad may include a bend stay wire within the extrusion and the extrusion may include two fluid lumens on either side equally spaced from a center lumen filled with solid metal. In some embodiments, the pad may be a balloon bonded to top and bottom, front and back. The pad may include lateral wings that expand, with flow within the wings. The pad may include a tubing taper length with same extrusion (e.g., 1 foot of small then 6 feet of large and/or without a seam or weld joint between large and small on internal lumens). In some embodiments, the distal end flow may pass through a channel. There may be one or more sections of the extrusion within the balloon that are below the top or bottom surface of the device and allow cross flow between lateral wings of the balloons.

The soft tissue cooling pads described herein may be constructed by any suitable technique. For example, in some embodiments, the distal end of the balloon may be inserted onto the distal end of the extrusion, heat sealed, and folded over itself inside out and heat sealed on the proximal neck side.

Example 13: Cooled Bone Fixation Plate

In this example, a cooled bone fixation plate (with pad to flow into plate reservoir) is described. The bone fixation plate may include a body comprising a first face that contacts bone and a second face opposite the first face, which does not contact bone, a reservoir formed inside the body, at least one open hole on the second face in fluid communication with the reservoir, a malleable pad insert having a distal end with sealing o-rings and 2 flow lumens to circulate fluid within the plate.

The example bone fixation plates can be used in any suitable method. For example, in some cases, a method of placing a bone plate [comprising the features described herein] includes anchoring the bone plate (to a bone or other feature) with fixation screws, connecting a thermal pad distal end into an open recess on the bone plate to form a closed loop circuit of fluid flow, and providing thermal therapy to adjacent neural elements.

Example 14: Cooled Retractor Sheath

In this example, a retractor blade having a cooling sheath is described. The retractor blade sheath includes a reservoir with a shape designed to match a retractor blade, a fluid diverting plug to fit within the reservoir, a channel within the plug for a retractor blade, and fluid conduits for inlet and exhaust from the plug into the reservoir. In some such embodiments, the internal walls of the sheath and the exterior faces of the retractor blade when plugged create a closed reservoir.

In some embodiments, the blade is flat metal. The opposing wide faces of the reservoir may be non-parallel. In some embodiments, a fluid conduit may be connected to the plug. The channel in the plug may be a C-channel and/or a 4-sided slot.

Example 15: Cooled Retractor Sheath (Wrap)

In this example, a retractor blade having a cooling sheath is described. The retractor blade sheath wrap includes a reservoir with a shape designed to accommodate a retractor blade and fluid conduits for inlet and exhaust from the reservoir. The blade may be flat or contoured and may be formed of metal or plastic.

The reservoir may be bonded along the proximal rim of the reservoir to the metal blade. A sealing element (such as an o-ring) may be located in the proximal rim opening of the reservoir. The sealing element may be sized to match the exterior circumference of the retractor blade. The sealing element may be assembled over the blade creating a fluid seal. In some embodiments, the sealing element may be sized larger than the exterior circumference of the retractor blade. In some such embodiments, the sealing element may be actuated to tighten around the blade, creating a fluid seal.

The described cooled retractor sheath may be used in accordance with the following example method. This example method includes removing the sheath from sterile packaging, inserting a retractor blade into the sheath, extending the sheath fully over the retractor blade to the sheath's full length, pushing the sealing element over the retractor blade to create a fluid seal (or, alternatively, actuating the larger sealing element), connecting a fluid tube extending from the sheath to a patient cooling system (or, alternatively, inserting/connecting the tube to a sheath exterior port and then connecting the fluid tube to the cooling system), and initiating a closed-loop fluid flow.

Example 16: Cooled Scope Sheath

In this example, a cooled scope sheath is described. The cooled scope sheath includes a reservoir membrane (cylindrically shaped or otherwise) assembled over a patient scope, and including fluid exhaust and inlet ports.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter described herein. The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

Example 17: Cooled Retractor Extension Shim

In this example, a Cooled Retractor Extension Shim is described. The Cooled Retractor Extension Shim exterior surfaces engage with the interior surfaces of a retractor blade. The cooled extension shim includes an internal fluid reservoir, fluid inlet and exhaust conduits and tubing in fluid communication with the refrigeration system in a closed-loop. The extension shim may have a blunt end, or it may have a pointed end. In some such embodiments, the shim is docked into spinal bone during surgery, or used to extend tissue retraction. Fluid tubing may enter the proximal end of the shim and interface with inlet and outlet exhaust ports. The ports may be present on a recessed surface. In some embodiments, fluid tubing may enter the flat posterior surface of the cooled shim. In some such embodiments, the fluid tubing may interface with the retractor blade, and may provide resistance for stability and positioning.

The extension shim may be used in conjunction with any tissue retraction to provide cooling to the distal end of the retractor and/or the tissue in direct contact with the cooled extension shim

What is claimed is:
1. A cooling system comprising:
a plurality of refrigeration units, wherein each refrigeration unit of the plurality of refrigeration units comprise:
a thermoelectric element in thermal communication with a heat exchanger;
a fluid pump in fluid communication with a fluid inlet and a fluid outlet;

tubing positioned within each of the refrigeration units of the plurality refrigeration units, wherein the tubing connects the fluid inlet to the fluid outlet;

a fluid cooling element in thermal contact with the thermoelectric element;

a fan; and a temperature sensor positioned to detect a temperature of fluid within the tubing;

wherein each of the refrigeration units of the plurality of refrigeration units is configured to comprise an independent closed-loop fluid circuit with a patient cooling device and a fluid cable and each of the refrigeration units of the plurality of refrigeration units are thermally independent from one another; and a control unit communicatively coupled with and configured to independently operate each of the refrigeration units of the plurality of refrigeration units, wherein the control unit comprises:

a user interface;

a power connector configured to provide power to the cooling system;

a power controller configured to adjust cooling power of the plurality of refrigeration units; and a power switch;

wherein the plurality of refrigeration units are configured to operatively interface with the control unit interchangeably at a plurality of discrete locations associated with the control unit; and wherein the fluid cable is configured to interface with at least one of the refrigeration units of the plurality of refrigeration units and the patient cooling device is configured to interface with the fluid cable.

2. The cooling system of claim 1, wherein the patient cooling device is at least one of a retractor blade with internal fluid paths, a bone screw with internal fluid paths, or a tissue cooling pad with internal fluid paths.

3. The cooling system of claim 1, wherein the fluid cooling element is in fluid contact with fluid within the tubing.

4. The cooling system of claim 1, wherein the fluid is a sterile liquid.

5. A method of applying thermal therapy to a target area of a patient tissue during surgery using the cooling system of claim 1, the method comprising:

connecting a power source to the cooling system;

connecting a tubing piece to at least one of the refrigeration units of the plurality of refrigeration units;

connecting the patient cooling device to the tubing piece, creating an independent closed-loop circuit between the at least one refrigeration unit of the plurality of refrigeration units, the tubing piece and the patient cooling device;

filling the tubing piece, the at least one refrigeration unit of the plurality of refrigeration units and the patient cooling device with a sterile fluid;

placing the patient cooling device in contact with the target area of patient tissue; and activating the cooling system to circulate the sterile fluid through the at least one refrigeration unit of the plurality of refrigeration units, the tubing piece, and the patient cooling device to cool the target area of patient tissue.

6. A method of filling the cooling system of claim 1 with a fluid to cool patient tissue during surgery, the method comprising:

connecting the power-connector to a power outlet;

connecting the patient cooling device to at least one of the refrigeration units of the plurality of refrigeration units using a tubing piece and a coupler with a plurality of fluid ports;

connecting a first fluid port on the coupler to a liquid source;

connecting a second fluid port on the coupler to a disposal vessel;

initiating a fill state in using the control unit, wherein the fluid fills the at least one refrigeration unit of the plurality of refrigeration units, the tubing piece and the patient cooling device;

terminating the fill state; and disconnecting the liquid source and the disposal vessel from the first fluid port and the second fluid port.

7. The method of claim 6, wherein the cooling system applies localized cooling after filling the system, and the method further comprises:

placing the patient cooling device at a target tissue site;

selecting a target cooling device temperature; and initiating cooling of patient tissue using the target cooling device temperature.

8. The method of claim 6, where the patient cooling device is placed at a target tissue site before filling begins.

9. The method of claim 6, further comprising:

expelling air out of the second fluid port, thereby creating a pressure difference between ambient air pressure and an inner pressure within the tubing piece.

10. The method of claim 6, wherein the tubing piece is pre-attached to at least one of the refrigeration units of the plurality of refrigeration units.

11. The method of claim 6, further comprising:

attaching the tubing piece to at least one of the refrigeration units of the plurality of refrigeration units.

12. The cooling system of claim 1, wherein each of the refrigeration units of the plurality of refrigeration units further comprise an internal sub-frame.

13. The cooling system of claim 12, wherein at least one of the thermoelectric element, the heat exchanger, the tubing, the fluid cooling element and the fan is configured to attach to the internal sub-frame.

14. The cooling system of claim 1, wherein each of the refrigeration units of the plurality of refrigeration units further comprise a refrigeration unit housing, wherein the refrigeration unit housing encompasses at least one of the thermoelectric element, the heat exchanger, the fluid pump, tubing, and fluid cooling element.

15. The cooling system of claim 14, wherein the thermoelectric element is configured to be at least partially surrounded by foam insulation.

16. The cooling system of claim 1, wherein at least one of the refrigeration units of the plurality of refrigeration units is configured to maintain a minimum voltage to the fan when power is connected to the cooling system.

17. The cooling system of claim 1, wherein each of the plurality of discrete locations comprise an electrical interface and a docking region configured to receive and connect to a refrigeration unit.

18. The cooling system of claim 17, wherein at least one of the plurality of refrigeration units is a cassette configured to be at least partially disposed within a respective docking region and mate with a respective electrical interface.

19. A cooling system comprising:

a plurality of refrigeration units, wherein each one of the plurality of refrigeration units comprise:

a thermoelectric element in thermal communication with a heat exchanger;

a fluid pump in fluid communication with a fluid inlet and a fluid outlet;

tubing positioned within the refrigeration unit, wherein
the tubing connects the fluid inlet to the fluid outlet;
a fluid cooling element in thermal contact with the
thermoelectric element;
a fan; and
a temperature sensor positioned to detect a temperature
of fluid within the tubing;
wherein each one of the plurality of refrigeration units is
configured to comprise a closed- loop fluid circuit with
a patient cooling device and a fluid cable and is
thermally independent from each other of the plurality
of refrigeration units;
a control unit communicatively coupled with and config-
ured to independently operate the plurality of refrig-
eration units, wherein the control unit comprises:
a user interface;
a plurality of slots;
wherein one of the plurality of refrigeration units is
configured to interface with one of the plurality of slots and the user interface is configured to reflect a
location of one of the plurality of refrigeration units
in the plurality of slots;
a power connector configured to provide power to the
cooling system;
a power controller configured to adjust cooling power
of the plurality of refrigeration units; and
a power switch;
wherein the fluid cable is configured to interface with at
least one of the plurality of refrigeration units and the
patient cooling device is configured to interface with
the fluid cable.

20. The cooling system of claim 19, wherein each of the
refrigeration units of the plurality of refrigeration units
interfacing with each slot of the plurality of slots has a
differing temperature.

* * * * *